United States Patent
Hoekstra et al.

(10) Patent No.: US 9,414,596 B2
(45) Date of Patent: Aug. 16, 2016

(54) METALLOENZYME INHIBITOR COMPOUNDS

(71) Applicant: Viamet Pharmaceuticals, Inc., Durham, NC (US)

(72) Inventors: William J. Hoekstra, Durham, NC (US); Robert J. Schotzinger, Raleigh, NC (US); Stephen W. Rafferty, West Palm Beach, FL (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 8 days.

(21) Appl. No.: 14/373,304

(22) PCT Filed: Jan. 18, 2013

(86) PCT No.: PCT/US2013/022317
§ 371 (c)(1),
(2) Date: Jul. 18, 2014

(87) PCT Pub. No.: WO2013/110002
PCT Pub. Date: Jul. 25, 2013

(65) Prior Publication Data
US 2015/0024938 A1    Jan. 22, 2015

Related U.S. Application Data

(60) Provisional application No. 61/589,064, filed on Jan. 20, 2012.

(51) Int. Cl.
| | |
|---|---|
| *A01N 43/713* | (2006.01) |
| *A01N 43/56* | (2006.01) |
| *A01N 43/653* | (2006.01) |
| *A01N 43/647* | (2006.01) |
| *A01N 57/16* | (2006.01) |

(52) U.S. Cl.
CPC .............. *A01N 43/713* (2013.01); *A01N 43/56* (2013.01); *A01N 43/647* (2013.01); *A01N 43/653* (2013.01); *A01N 57/16* (2013.01)

(58) Field of Classification Search
CPC . A01N 43/713; A01N 43/647; A01N 43/653; A01N 43/56; A01N 57/16
See application file for complete search history.

(56) References Cited

U.S. PATENT DOCUMENTS

| | | | |
|---|---|---|---|
| 4,616,026 A | 10/1986 | Richardson et al. | |
| 5,624,916 A | 4/1997 | Shaber et al. | |
| 5,998,455 A | 12/1999 | Knauf-Beiter et al. | |
| 8,940,735 B2 * | 1/2015 | Hoekstra ................ | A61K 45/06 514/229.2 |
| 2011/0306644 A1 | 12/2011 | Hoekstra et al. | |

FOREIGN PATENT DOCUMENTS

| | | |
|---|---|---|
| WO | WO-2010025832 A1 | 3/2010 |
| WO | WO 2012/177728 A1 | 12/2012 |

OTHER PUBLICATIONS

International Search Report of PCT/US2013/022317, dated Apr. 29, 2013.
Extended European Search Report mailed Jun. 23, 2015 in connection with EP 13739106.6.
Hoekstra et al., Design and optimization of highly-selective fungal CYP51 inhibitors. c. doi: 10.1016/j.bmcl.2014.05.068. Epub Jun. 9, 2014.

\* cited by examiner

*Primary Examiner* — John Pak
(74) *Attorney, Agent, or Firm* — Wolf, Greenfield & Sacks, P.C.

(57) ABSTRACT

The present disclosure describes compounds having agricultural fungicidal activity.

21 Claims, No Drawings

METALLOENZYME INHIBITOR COMPOUNDS

CROSS-REFERENCE TO RELATED APPLICATIONS

This application is the National Phase under 35 U.S.C. §371 of PCT International Application No. PCT/US2013/022317, filed Jan. 18, 2013, which claims the benefit of U.S. Provisional Application No. 61/589,064 filed Jan. 20, 2012, the contents of which are incorporated herein by reference in their entirety.

BACKGROUND

Fungicides are compounds, of natural or synthetic origin, which act to protect and cure plants against damage caused by agriculturally relevant fungi. Generally, no single fungicide is useful in all situations. Consequently, research is ongoing to produce fungicides that may have better performance, are easier to use, and cost less.

The present disclosure relates to compounds of Formula I, shown below, and their derivatives and their use as fungicides. The compounds of the present disclosure may offer protection against ascomycetes, basidiomycetes, deuteromycetes and oomycetes.

BRIEF SUMMARY OF THE INVENTION

A method of controlling a pathogen-induced disease in a plant that is at risk of being diseased from the pathogen comprising contacting one of the plant and an area adjacent to the plant with a composition of Formula I or a salt, solvate, hydrate, or prodrug thereof, wherein:

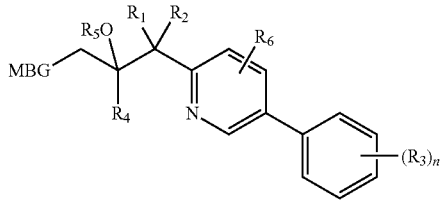

(I)

MBG is optionally substituted tetrazolyl, optionally substituted triazolyl, or optionally substituted pyrazolyl;
$R_1$ is H, halo, alkyl or haloalkyl;
$R_2$ is H, halo, alkyl or haloalkyl;
$R_3$ is independently H, alkyl, cyano, haloalkyl, alkoxy, halo, haloalkoxy, cycloalkyl, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino);
$R_4$ is heteroaryl or cycloalkyl, optionally substituted with 0, 1, 2 or 3 independent $R_3$;
$R_5$ is H, $-P(O)(OH)_2$, $-CH_2-O-P(O)(OH)_2$, or $-C(O)$alkyl optionally substituted with amino;
$R_6$ is H, halo, alkyl, haloalkyl or haloalkoxy;
$R_7$ is alkyl or cycloalkyl;
$R_8$ is alkyl or haloalkyl; and
n is 0, 1, 2 or 3.

Another aspect is a composition of Formula I or a salt, solvate hydrate or prodrug thereof wherein

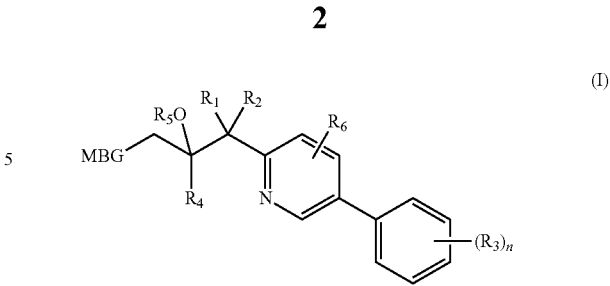

(I)

MBG is optionally substituted tetrazolyl, optionally substituted triazolyl, or optionally substituted pyrazolyl;
$R_1$ is H, halo, alkyl or haloalkyl;
$R_2$ is H, halo, alkyl or haloalkyl;
$R_3$ is independently H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino);
$R_4$ is aryl, heteroaryl or cycloalkyl, optionally substituted with 0, 1, 2 or 3 independent $R_3$;
$R_5$ is H, $-P(O)(OH)_2$, $-CH_2-O-P(O)(OH)_2$, or $-C(O)$alkyl optionally substituted with amino;
$R_6$ is halo, alkyl, haloalkyl or haloalkoxy;
$R_7$ is alkyl or cycloalkyl;
$R_8$ is alkyl or haloalkyl; and
n is 0, 1, 2 or 3.

Another aspect is a composition of Formula I or a salt, solvate hydrate or prodrug thereof wherein

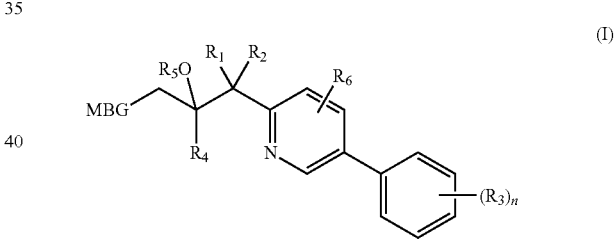

(I)

MBG is optionally substituted tetrazolyl, optionally substituted triazolyl, or optionally substituted pyrazolyl;
$R_1$ is H, halo, alkyl or haloalkyl;
$R_2$ is H, halo, alkyl or haloalkyl;
$R_3$ is independently H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino);
$R_4$ is aryl, heteroaryl or cycloalkyl, optionally substituted with 0, 1, 2 or 3 independent $R_3$;
$R_5$ is H, $-P(O)(OH)_2$, $-CH_2-O-P(O)(OH)_2$, or $-C(O)$alkyl optionally substituted with amino;
$R_6$ is hydrogen, halo, alkyl, haloalkyl or haloalkoxy;
$R_7$ is alkyl or cycloalkyl;
$R_8$ is alkyl or haloalkyl; and
n is 0, 1, 2 or 3.

Another aspect is a composition of Formula I or a salt, solvate hydrate or prodrug thereof wherein

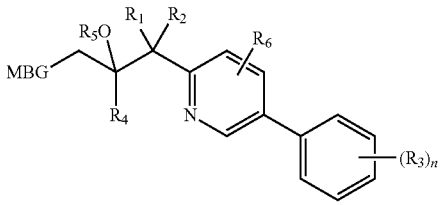

(I)

MBG is optionally substituted tetrazolyl, optionally substituted triazolyl, or optionally substituted pyrazolyl;

$R_1$ is H, halo, alkyl or haloalkyl;

$R_2$ is H, halo, alkyl or haloalkyl;

$R_3$ is independently H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino), $NHC(=O)CF_3$, or $OCF_2C(=O)OR_7$;

$R_4$ is aryl, heteroaryl or cycloalkyl, optionally substituted with 0, 1, 2 or 3 independent $R_3$;

$R_5$ is H, —$P(O)(OH)_2$, —$CH_2$—O—$P(O)(OH)_2$, or —C(O)alkyl optionally substituted with amino;

$R_6$ is hydrogen, halo, alkyl, haloalkyl or haloalkoxy;

$R_7$ is hydrogen, alkyl or cycloalkyl;

$R_8$ is hydrogen, alkyl or haloalkyl; and n is 0, 1, 2 or 3.

Another aspect is a compound of the formulae herein, wherein the MBG is an optionally substituted 1H-tetrazol-1-yl, optionally substituted 2H-tetrazol-2-yl, optionally substituted 1H-1,2,4-triazol-1-yl, optionally substituted 1H-1,2,3-triazol-1-yl, or optionally substituted 1H-pyrazol-3-yl.

Another aspect is a compound of the formulae herein, wherein the MBG is unsubstituted 1H-tetrazol-1-yl, unsubstituted 2H-tetrazol-2-yl, unsubstituted 1H-1,2,4-triazol-1-yl, unsubstituted 1H-1,2,3-triazol-1-yl, or unsubstituted 1H-pyrazol-3-yl.

Another aspect is a compound of the formulae herein, wherein the compound is not 4-(6-(2-(2,4-Difluorophenyl)-1,1-difluoro-2-hydroxy-3-(1H-tetrazol-1-yl)propyl)pyridin-3-yl)phenol (23) or 2-(2,4-Difluorophenyl)-1,1-difluoro-3-(1H-tetrazol-1-yl)-1-(5-(4-((trifluoromethyl)thio)phenyl)pyridin-2-yl)propan-2-ol (27).

Another aspect is a compound of the formulae herein, wherein the MBG is 1H-tetrazol-1-yl.

Another aspect is a compound of the formulae herein, wherein $R_1$ is fluoro.

Another aspect is a compound of the formulae herein, wherein $R_2$ is fluoro.

Another aspect is a compound of the formulae herein, wherein $R_1$ and $R_2$ are fluoro.

Another aspect is a compound of the formulae herein, wherein $R_1$ is alkyl.

Another aspect is a compound of the formulae herein, wherein $R_1$ is methyl.

Another aspect is a compound of the formulae herein, wherein $R_1$ is methyl and $R_2$ is fluoro.

Another aspect is a compound of the formulae herein, wherein $R_3$ is independently cycloalkyl, alkoxyalkyl, haloalkoxyalkyl, aryloxyalkyl, thioalkyl, thiocyanate, $S(O)_2R_7$, nitro, $C(=O)CF_3$, $C(=O)OR_7$, $C(=O)NR_7R_8$, amino, cyclic amino.

Another aspect is a compound of the formulae herein, wherein $R_4$ is phenyl optionally substituted with 0, 1, 2 or 3 independent $R_3$.

Another aspect is a compound of the formulae herein, wherein $R_4$ is phenyl optionally substituted with 0, 1, 2 or 3 independent halo.

Another aspect is a compound of the formulae herein, wherein $R_4$ is phenyl optionally substituted with 0, 1, 2 or 3 independent fluoro.

Another aspect is a compound of the formulae herein, wherein $R_4$ is 2,4-difluorophenyl.

Another aspect is a compound of the formulae herein, wherein $R_5$ is H.

Another aspect is a compound of the formulae herein, wherein $R_5$ is amino substituted acyl.

Another aspect is a compound of the formulae herein, wherein $R_6$ is H.

Another aspect is a compound of the formulae herein, wherein $R_6$ is halo, alkyl, haloalkyl or haloalkoxy.

Another aspect is a compound of the formulae herein, wherein n is 1, 2 or 3.

Another aspect is a compound of the formulae herein, wherein:

$R_1$ is fluoro;
$R_2$ is fluoro;
$R_4$ is 2,4-difluorophenyl; and
$R_5$ is H.

Another aspect is a compound of the formulae herein, wherein:

each $R_3$ is independently cyano, haloalkyl, alkoxy, halo, haloalkoxy, and
n is 1 or 2.

Another aspect is a compound of the formulae herein, wherein:

each $R_3$ is independently cyano, haloalkyl, alkoxy, halo, haloalkoxy, and
n is 1.

Another aspect is a compound of the formulae herein, wherein:

each $R_3$ is independently cyano, haloalkyl, alkoxy, halo, haloalkoxy, and
n is 1.

Another aspect is a compound of the formulae herein, wherein:

$R_1$ is methyl;
$R_2$ is fluoro; and
$R_3$ is independently H, alkyl, cyano, haloalkyl, alkoxy, halo, haloalkoxy, cycloalkyl, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino).

Another aspect is a compound of the formulae herein, wherein:

each $R_3$ is independently alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, cyclic amino (such as morpholino, pyrrolidino, piperidino, N-alkyl piperidino), and
n is 1.

Another aspect is a compound of the formulae herein, wherein:

each $R_3$ is independently H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)$ NR$_7$R$_8$, amino, cyclic amino (such as morpholino, pyrrolidino, piperidino, N-alkyl piperidino), and
n is 1 or 2.

Another aspect is a compound of the formulae herein, wherein:
  each R$_3$ is independently 4-cyano, 4-trifluoromethyl, 3-cyano, 4-isopropoxy, 4-fluoro, 3-trifluoromethoxy, 4-trifluoromethoxy, 3-chloro, 4-chloro, 2-fluoro, 5-fluoro, 4-(2,2,2-trifluoroethoxy), 4-(3,3,3-trifluoro, 2,2-difluoropropoxy), 2,5-difluoro, 3-fluoro, 4-hydroxy, 3-isopropyl, 3,4-difluoro, 3-difluoromethoxy, 4-trifluoromethylthio, 4-t-butoxy, 4-chloro-3-fluoro, 3-hydroxy, 3-trifluoromethyl, 4-nitro, 4-trifluoromethylcarbonyl, H, 4-morpholino, 4-(trifluoroacetamido), 4-(difluoromethoxy), 4-(difluoromethylthio), 4-(2,2,2-trifluoroethyl), 4-(methylamido), 4-(-O—CF$_2$C(O)OEt), 4-(3,3,3-trifluoropropoxy), or 4-(2,2,2-trifluoroethylthio).

In certain instances, the compounds of the invention are selected from the following of Formula I (and agriculturally acceptable salts, solvates, or hydrates thereof):

4-(6-(2-(2,4-Difluorophenyl)-1,1-difluoro-2-hydroxy-3-(1H-tetrazol-1-yl)propyl)pyridin-3-yl)benzonitrile (1);
2-(2,4-Difluorophenyl)-1,1-difluoro-3-(1H-tetrazol-1-yl)-1-(5-(4-(trifluoromethyl)phenyl)pyridin-2-yl) propan-2-ol (2);
3-(6-(2-(2,4-Difluorophenyl)-1,1-difluoro-2-hydroxy-3-(1H-tetrazol-1-yl)propyl)pyridin-3-yl)benzonitrile (3);
2-(2,4-Difluorophenyl)-1,1-difluoro-1-(5-(4-isopropoxyphenyl)pyridin-2-yl)-3-(1H-tetrazol-1-yl)propan-2-ol (4);
2-(2,4-Difluorophenyl)-1,1-difluoro-1-(5-(4-fluorophenyl)pyridin-2-yl)-3-(1H-tetrazol-1-yl)propan-2-ol (5);
2-(2,4-Difluorophenyl)-1,1-difluoro-3-(1H-tetrazol-1-yl)-1-(5-(3-(trifluoromethoxy)phenyl)pyridin-2-yl)propan-2-ol (6);
2-(2,4-Difluorophenyl)-1,1-difluoro-3-(1H-tetrazol-1-yl)-1-(5-(4-(trifluoromethoxy) phenyl)pyridin-2-yl) propan-2-ol (7);
1-(5-(3-Chlorophenyl)pyridin-2-yl)-2-(2,4-difluorophenyl)-1,1-difluoro-3-(1H-tetrazol-1-yl)propan-2-ol (8);
1-(5-(4-Chlorophenyl)pyridin-2-yl)-2-(2,4-difluorophenyl)-1,1-difluoro-3-(1H-tetrazol-1-yl)propan-2-ol (9);
2-(2,4-Difluorophenyl)-1-(5-(2,5-difluorophenyl)pyridin-2-yl)-1,1-difluoro-3-(1H-tetrazol-1-yl)propan-2-ol (10);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11);
2-(2,4-Difluorophenyl)-1,1-difluoro-1-(5-(4-(2,2,3,3,3-pentafluoropropoxy)phenyl)pyridin-2-yl)-3-(1H-tetrazol-1-yl)propan-2-ol (12);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate hydrochloride (13);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14);
2-(2,4-Difluorophenyl)-1,1-difluoro-3-(1H-pyrazol-3-yl)-1-(5-(4-(trifluoromethoxy) phenyl)pyridin-2-yl) propan-2-ol (15);
2-(2,4-Difluorophenyl)-1,1-difluoro-1-(5-(4-fluorophenyl)pyridin-2-yl)-3-(1H-1,2,4-triazol-1-yl)propan-2-ol (16);
2-(2,4-Difluorophenyl)-1,1-difluoro-3-(1H-1,2,4-triazol-1-yl)-1-(5-(4-(2,2,2-trifluoroethoxy)phenyl)pyridin-2-yl) propan-2-ol (17);
2-(2,4-Difluorophenyl)-1,1-difluoro-3-(1H-1,2,4-triazol-1-yl)-1-(5-(4-(trifluoromethoxy) phenyl)pyridin-2-yl)propan-2-ol (18);
2-(2,4-Difluorophenyl)-1,1-difluoro-3-(1H-1,2,3-triazol-1-yl)-1-(5-(4-(trifluoromethoxy) phenyl)pyridin-2-yl)propan-2-ol (19);
2-(2,4-Difluorophenyl)-1,1-difluoro-3-(2H-tetrazol-2-yl)-1-(5-(4-(2,2,2-trifluoroethoxy)phenyl)pyridin-2-yl)propan-2-ol (20);
2-(2,4-Difluorophenyl)-1,1-difluoro-1-(5-(3-(fluorophenyl)pyridin-2-yl)-3-(2H-tetrazol-2-yl)propan-2-ol (21);
2-(2,4-Difluorophenyl)-1,1-difluoro-3-(2H-tetrazol-2-yl)-1-(5-(4-(trifluoromethylphenyl) pyridin-2-yl)propan-2-ol (22);
4-(6-(2-(2,4-Difluorophenyl)-1,1-difluoro-2-hydroxy-3-(1H-tetrazol-1-yl)propyl)pyridin-3-yl)phenol (23);
2-(2,4-Difluorophenyl)-1,1-difluoro-1-(5-(3-isopropylphenyl)pyridin-2-yl)-3-(1H-tetrazol-1-yl)propan-2-ol (24);
2-(2,4-Difluorophenyl)-1-(5-(3,4-difluorophenyl)pyridin-2-yl)-1,1-difluoro-3-(1H-tetrazol-1-yl)propan-2-ol (25);
1-(5-(3-(Difluoromethoxy)phenyl)pyridin-2-yl)-2-(2,4-difluorophenyl)-1,1-difluoro-3-(1H-tetrazol-1-yl)propan-2-ol (26);
2-(2,4-Difluorophenyl)-1,1-difluoro-3-(1H-tetrazol-1-yl)-1-(5-(4-((trifluoromethyl)thio)phenyl)pyridin-2-yl)propan-2-ol (27);
1-(5-(4-(tert-Butoxy)phenyl)pyridin-2-yl)-2-(2,4-difluorophenyl)-1,1-difluoro-3-(1H-tetrazol-1-yl)propan-2-ol (28);
1-(5-(4-Chloro-3-fluorophenyl)pyridin-2-yl)-2-(2,4-difluorophenyl)-1,1-difluoro-3-(1H-tetrazol-1-yl)propan-2-ol (29);
3-(6-(2-(2,4-Difluorophenyl)-1,1-difluoro-2-hydroxy-3-(1H-tetrazol-1-yl)propyl)pyridin-3-yl)phenol (30);
2-(2,4-Difluorophenyl)-1,1-difluoro-3-(1H-tetrazol-1-yl)-1-(5-(3-(trifluoromethyl)phenyl)pyridin-2-yl)propan-2-ol (31);
2-(2,4-Difluorophenyl)-1,1-difluoro-1-(5-(4-nitrophenyl)pyridin-2-yl)-3-(1H-tetrazol-1-yl)propan-2-ol (32);
1-(4-(6-(2-(2,4-Difluorophenyl)-1,1-difluoro-2-hydroxy-3-(1H-tetrazol-1-yl)propyl)pyridin-3-yl)phenyl)-2,2,2-trifluoroethanone (33);
2-(4-Chloro-2-fluorophenyl)-1,1-difluoro-3-(1H-tetrazol-1-yl)-1-(5-(4-(trifluoromethoxy)phenyl)pyridin-2-yl)propan-2-ol (34);
2-(2,4-Difluorophenyl)-1,1-difluoro-1-(5-phenylpyridin-2-yl)-3-(1H-tetrazol-1-yl)propan-2-ol (35);
2-(2,4-Difluorophenyl)-1,1-difluoro-1-(5-(4-morpholinophenyl)pyridin-2-yl)-3-(1H-tetrazol-1-yl)propan-2-ol (36);
N-(4-(6-(2-(2,4-Difluorophenyl)-1,1-difluoro-2-hydroxy-3-(1H-tetrazol-1-yl)propyl)pyridin-3-yl)phenyl)-2,2,2-trifluoroacetamide (37);
1-(5-(4-(Difluoromethoxy)phenyl)pyridin-2-yl)-2-(2,4-difluorophenyl)-1,1-difluoro-3-(1H-tetrazol-1-yl)propan-2-ol (38);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (39);
1-(5-(4-((Difluoromethyl)thio)phenyl)pyridin-2-yl)-2-(2,4-difluorophenyl)-1,1-difluoro-3-(1H-tetrazol-1-yl)propan-2-ol (40);
2-(2,4-Difluorophenyl)-1,1-difluoro-3-(1H-tetrazol-1-yl)-1-(5-(4-(2,2,2-trifluoroethyl)phenyl)pyridin-2-yl)propan-2-ol (41);
4-(6-(2-(2,4-Difluorophenyl)-1,1-difluoro-2-hydroxy-3-(1H-tetrazol-1-yl)propyl)pyridin-3-yl)-N-methylbenzamide (42);

Ethyl 2-(4-(6-(2-(2,4-difluorophenyl)-1,1-difluoro-2-hydroxy-3-(1H-tetrazol-1-yl)propyl)pyridin-3-yl)phenoxy)-2,2-difluoroacetate (43);
2-(2,4-Difluorophenyl)-1,1-difluoro-3-(1H-tetrazol-1-yl)-1-(5-(4-(3,3,3-trifluoropropoxy)phenyl)pyridin-2-yl)propan-2-ol (44);
2-(2,4-Difluorophenyl)-1,1-difluoro-3-(1H-tetrazol-1-yl)-1-(5-(4-((2,2,2-trifluoroethyl)thio)phenyl)pyridin-2-yl)propan-2-ol (45);
2-(2,4-Difluorophenyl)-3-fluoro-1-(1H-tetrazol-1-yl)-3-(5-(4-(trifluoromethoxy)phenyl)pyridin-2-yl)butan-2-ol (46 and 47);
2-(2,4-Difluorophenyl)-3-fluoro-3-(5-(4-fluorophenyl)pyridin-2-yl)-1-(2H-tetrazol-2-yl)butan-2-ol (48 and 49);
2-(2,4-Difluorophenyl)-3-fluoro-3-(5-(4-fluorophenyl)pyridin-2-yl)-1-(1H-tetrazol-1-yl)butan-2-ol (50 and 51);
2-(2,4-Difluorophenyl)-3-fluoro-1-(1H-tetrazol-1-yl)-3-(5-(4-(trifluoromethyl)phenyl)pyridin-2-yl)butan-2-ol (52 and 53);
3-(5-(4-Chlorophenyl)pyridin-2-yl)-2-(2,4-difluorophenyl)-3-fluoro-1-(1H-tetrazol-1-yl)butan-2-ol (54 and 55);
2-(2,4-Difluorophenyl)-3-fluoro-1-(1H-tetrazol-1-yl)-3-(5-(4-(2,2,2-trifluoroethoxy)phenyl)pyridin-2-yl)butan-2-ol (56 and 57)
2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl dihydrogen phosphate (58).

In another aspect, the invention provides an agricultural composition comprising the compound of Formula I and an agriculturally acceptable carrier.

DETAILED DESCRIPTION

Definitions

In order that the invention may be more readily understood, certain terms are first defined here for convenience.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "agriculturally effective amount" refers to that amount of the compound being administered sufficient to prevent development of or alleviate to some extent one or more of the symptoms of the condition or disorder being treated.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used throughout this specification, the term 'R' refers to the group consisting of $C_{1-8}$ alkyl, $C_{3-8}$ alkenyl or $C_{3-8}$ alkynyl, unless stated otherwise.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —OR substituent where R. is $C_{1-8}$ alkyl, $C_{3-8}$ alkenyl or $C_{3-8}$ alkynyl, unless stated otherwise.

As used herein, the term "halogen", "hal" or "halo" means —F, —Cl, —Br or —I.

The term "haloalkoxy" refers to an —OR substituent where R is fully or partially substituted with Cl, F, I, or Br or any combination thereof. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of a cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g.

*Design And Optimization in Organic Synthesis*, 2nd Edition, Carlson R, Ed, 2005; Elsevier Science Ltd.; Jähnisch, K. et al., *Angew. Chem. Int. Ed. Engl.* 2004, 43, 406; and references therein). Additional reaction schemes and protocols may be determined by the skilled artisan by use of commercially available structure-searchable database software, for instance, SciFinder® (CAS division of the American Chemical Society) and CrossFire Beilstein®(Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms; in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Compounds of Formula I may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Compounds of Formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Suitable salts include those derived from alkali or alkaline earth metals and those derived from ammonia and amines. Preferred cations include sodium, potassium, magnesium, and aminium cations of the formula:

wherein $R^9$, $R^{10}$, $R^{11}$ and $R^{12}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^9$, $R^{10}$, $R^{11}$ and $R^{12}$ are sterically compatible. Additionally, any two of $R^9$, $R^{10}$, $R^{11}$ and $R^{12}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula I because they are water-soluble and lend themselves to the preparation of desirable aqueous based herbicidal compositions.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds and compositions herein may be used in methods of preventing or controlling pathogen induced diseases on a plant comprising contacting a compound herein with the plant (e.g., seed, seedling, grass, weed, grain) or an area adjacent to the plant. The compounds and compositions herein may be used to treat a plant, field or other agricultural area by administering the compound or composition (e.g., contacting, applying, spraying, atomizing, dusting, etc.) to the subject plant, field or other agricultural area. The administration may be either pre- or post-emergence. The administration may be either as a treatment or preventative regimen. As such, the compounds, compositions and agricultural uses herein include lawn, turf, ornamental vegetation, home and garden, farming, range and pasture applications. The pathogen may be any on a plant and include those delineated herein.

One embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants Preferably, the compounds of the present disclosure are applied in the form of a formulation, comprising one or more of the compounds of Formula I with an agriculturally or phytologically acceptable carrier. The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The present disclosure contemplates all vehicles by which one or more of the compounds may be formulated for delivery and use as a fungicide. Typically, formulations are applied as aqueous suspensions or emulsions. Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cottonseed, walnut, palm, castor, earth almond, hazelnut, avocado, sesame, *croton tiglium*, cacao, linseed, rapeseed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodium carboxymethylcellulose, ethyl cellulose, hydroxypropyl methyl cellulose, and mixtures thereof.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephon, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

The compositions of Formula I may be effective against pathogen induced diseases where the plant fungal pathogen belonging to at least one genera selected from *Blumeria, Podosphaera, Sphaerotheca, Uncinula, Erysiphe, Puccinia, Phakopsora, Gymnosporangium, Hemileia, Uromyces, Alternaria, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminthosporium, Stagonospora, Exserohilum*, and *Pyricularia*. Pathogens such as *Venturia inaequalis, Septoria tritici, Cercospora beticola, Cercospora arachidicola, Colletotrichum lagenarium, Puccinia graminis f. sp. tritici, Uncinula necator, Blumeria graminis*, and *Mycosphaerella fijiensis* may be controlled by compositions of Formula I. Additionally, the compositions of Formula 1 may be effective in preventing or controlling diseases including apple scab, speckled leaf blotch of wheat, leaf spot of sugarbeets, leaf spot of peanut, cucumber anthracnose, wheat leaf rust, grape powdery mildew, wheat powdery mildew, and black sigatoka.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound of Formula I; such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

The compounds of the present disclosure may be effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Antifungals

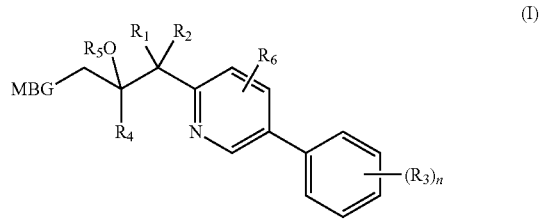

Syntheses of azole targets (I) may be accomplished using the example synthesis that is shown below (Scheme 1). A broad range of arenes and heterocycles, in addition to the 2-pyridine example below, may be prepared starting from functionalized halo-aromatic starting materials (e.g. 1). For the purpose of this example, R4 is a halogenated benzene moiety. An example synthesis of targets (I) commences with condensation of A with copper-activated ethyl α-bromo-difluoroacetate followed by condensation of the incipient ethyl ester product with lithiated bromodifluorobenzene to furnish ketone B (Scheme 1). The ketone is epoxidized with diazomethane to afford C. The bromo-pyridine intermediate C may be treated with aryl-boronic acids to introduce the R3-Ph moiety of D. The product D is obtained by then opening the epoxide with azole in the presence of a base such as potassium carbonate.

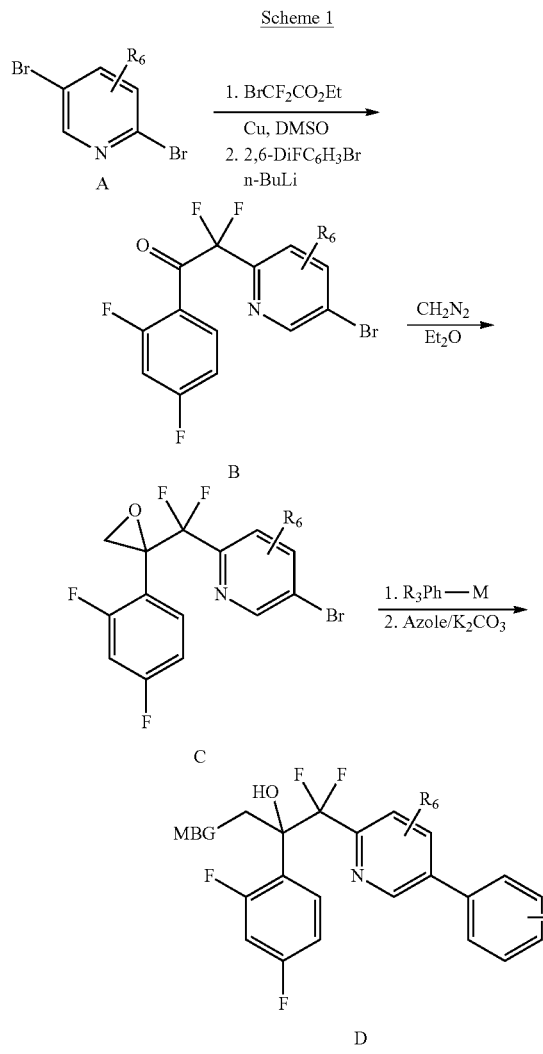

Synthesis of 2-(5-Bromopyridin-2-yl)-1-(2,4-difluorophenyl)-2,2-difluoroethanone (B)

To a suspension of copper powder (2.68 grams (g), 42.2 millimoles (mmol)) in dimethyl sulfoxide (DMSO; 35 milliliters (mL)) was added ethyl bromodifluoroacetate (2.70 mL, 21.10 mmol), and the mixture was stirred for 1 hour (h) at room temperature (RT). 2,5-Dibromopyridine (2.50 g, 10.55 mmol) was then added and stirring was continued for 15 h at RT. The reaction was quenched with aqueous ammonium chloride ($NH_4Cl$) and was extracted with dichloromethane ($CH_2Cl_2$; 3×25 mL). The combined organic layers were washed with water, washed with brine, dried over anhydrous sodium sulfate ($Na_2SO_4$), and concentrated under reduced pressure to afford crude product mixture which upon column purification using ethyl acetate (EtOAc)/hexane afforded the ethyl ester intermediate (2.40 g, 8.57 mmol, 81%) as a pale yellow oil. $^1$H NMR (500 MHz, $CDCl_3$): δ 8.71 (s, 1H), 8.00 (d, J=9.0 Hz, 1H), 7.64 (d, J=9.0 Hz, 1H), 4.42-4.35 (m, 2H), 1.39-1.31 (m, 3H).

To a stirred solution of 1-bromo-2,4-difluorobenzene (1.65 g, 8.57 mmol) in diethyl ether (10 mL) was added n-butyllithium (n-BuLi; 3.70 mL, 8.57 mmol) at −70° C., followed by addition of the ethyl ester from above (2.40 g, 8.57 mmol) in diethyl ether (5 mL) after 15 minutes (min). The reaction mixture was stirred for 1 h at −70° C. and was warmed to room temperature at which point the mixture was stirred for another 2 h. The reaction was quenched with aqueous $NH_4Cl$ solution and extracted with EtOAc (3×20 mL). The combined organic layers were washed with water, washed with brine, dried over anhydrous $Na_2SO_4$, and concentrated under reduced pressure. The crude compound was purified by column chromatography to afford ketone B (1.30 g, 3.73 mmol, 43%) as yellow liquid. $^1$H NMR (500 MHz, $CDCl_3$): δ 8.62 (s, 1H), 8.08-8.04 (m, 2H), 7.74-7.70 (m, 1H), 7.05-6.95 (m, 1H), 6.88-6.78 (m, 1H). MS (ESI): 347, 349 [$(M^+ +1)+2$].

5-Bromo-2-((2-(2,4-difluorophenyl)oxiran-2-yl)difluoromethyl)pyridine (C)

To a stirred solution of ketone B (1.30 g, 3.73 mmol) in diethyl ether (300 mL) was added freshly prepared diazomethane at 0° C. followed by warming to RT. The reaction mixture was stirred for 2 h. The volatiles were removed under reduced pressure to afford a crude product mixture which upon column chromatography using EtOAc/hexane as the eluent afforded oxirane C (800 mg, 2.20 mmol, 59%) as light yellow solid. $^1$H NMR (500 MHz, $CDCl_3$): δ 8.72 (s, 1H), 7.89 (d, J=9.0 Hz, 1H), 7.39-7.35 (m, 2H), 6.86-6.83 (m, 1H), 6.77-6.74 (m, 1H), 3.44 (s, 1H), 2.98 (s, 1H). MS (ESI): 362, 364 [$(M^+ +1)+2$].

Example 1

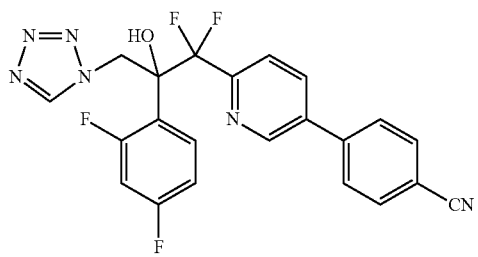 [SMILES: N#Cc1ccc(-c2ccc(C(F)(F)C(O)(Cn3cnnn3)c3ccc(F)cc3F)nc2)cc1]

4-(6-(2-(2,4-Difluorophenyl)-1,1-difluoro-2-hydroxy-3-(1H-tetrazol-1-yl)propyl)pyridin-3-yl)benzonitrile (1)

To a stirred solution of epoxide C (0.3 g, 0.82 mmol) and 4-cyano-benzene boronic acid (0.14 g, 0.99 mmol) in 1,4-dioxane (5 mL) was added potassium carbonate ($K_2CO_3$; 0.17 g, 1.24 mmol) at RT under an inert atmosphere. After purging with argon for a period of 30 min, 1,1′-Bis(diphenylphosphino)ferrocene]dichloropalladium(II) ($Pd(dppf)_2Cl_2$; 30 mg, 0.041 mmol) was added to the reaction mixture under argon atmosphere. The resulting mixture was stirred for 8 h at 75° C. Progress of the reaction was monitored by thin layer chromatography (TLC). The solvent was evaporated under reduced pressure; the obtained residue was dissolved in water (20 mL). The aqueous layer was extracted with EtOAc (3×50 mL). The combined organic phases were washed with water and brine, dried over anhydrous $Na_2SO_4$ and concentrated. The crude material was purified by column chromatography to afford coupled product (0.15 g, 0.39 mmol, 47%) as a solid. $^1$H NMR (500 MHz, CDCl$_3$): δ 8.87 (s, 1H), 7.95 (dd, J=8.0, 2.0 Hz, 1H), 7.81-7.77 (m, 2H), 7.71-7.68 (m, 2H), 7.61 (d, J=8.0 Hz, 1H), 7.43 (app q, 1H), 6.87-6.83 (m, 1H), 6.77-6.73 (m, 1H), 3.48 (d, J=5.0 Hz, 1H), 3.00 (app s, 1H). MS (ESI): m/z 385 [M$^+$+1].

To a stirred solution of the coupled product (150 mg, 0.39 mmol) in N,N-dimethylformamide (DMF; 3 mL) were added 1H-tetrazole (33 mg, 0.46 mmol) followed by K$_2$CO$_3$ (27 mg, 0.19 mmol) at RT under an inert atmosphere. The reaction mixture was stirred for 16 h at 70° C. The reaction mixture was cooled to RT, diluted with water (5 mL) and extracted with EtOAc (2×20 mL). The organic layer was washed with water and brine and dried over anhydrous Na$_2$SO$_4$. After filtering off the solid, the solvent was evaporated under reduced pressure to give crude compound. The crude compound was purified by column chromatography to afford compound 1 (50 mg, 0.11 mmol, 28%) as a white solid. $^1$H NMR (500 MHz, CDCl$_3$): δ 8.75 (s, 1H), 8.71 (s, 1H), 8.00 (dd, J=8.0, 2.0 Hz, 1H), 7.82 (d, J=7.0 Hz, 2H), 7.72 (d, J=8.5 Hz, 1H), 7.67 (d, J=7.0 Hz, 2H), 7.44-7.39 (m, 1H), 7.37 (s, 1H), 6.81-6.77 (m, 1H), 6.72-6.68 (m, 1H), 5.53 (d, J=14.5 Hz, 1H), 5.20 (d, J=14.5 Hz, 1H). HPLC: 99.6%. MS (ESI): m/z 455 [M$^+$+1].

Example 2

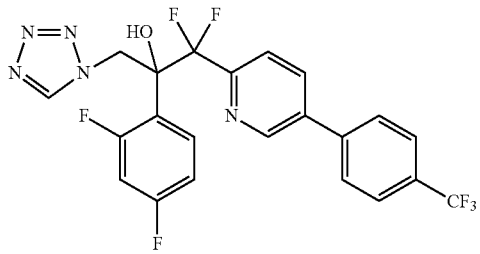 [SMILES: OC(Cn1cnnn1)(c1ccc(F)cc1F)C(F)(F)c1ccc(-c2ccc(C(F)(F)F)cc2)cn1]

2-(2,4-Difluorophenyl)-1,1-difluoro-3-(1H-tetrazol-1-yl)-1-(5-(4-(trifluoromethyl)phenyl)pyridin-2-yl)propan-2-ol (2)

To a stirred solution of bromo-epoxide C (0.25 g, 0.69 mmol) in tetrahydrofuran (THF; 20 mL) and water (7 mL) were added 4-(trifluoromethyl)phenylboronic acid (0.10 g, 0.55 mmol), sodium carbonate (Na$_2$CO$_3$; 0.16 g, 1.55 mmol) and Pd(dppf)$_2$Cl$_2$ (0.14 g, 0.17 mmol) at RT under an inert atmosphere. After purging with argon for a period of 30 min, the reaction mixture was heated to 75° C. and stirring was continued for 4 h. Progress of the reaction was monitored by TLC. The reaction mixture was cooled to RT and filtered through a pad of celite. The filtrate was concentrated under reduced pressure, and the obtained residue was dissolved in EtOAc (30 mL). The organic layer was washed with water and brine, was dried over anhydrous Na$_2$SO$_4$, and was concentrated under reduced pressure. The crude compound was purified by column chromatography to afford coupled product (0.21 g, 0.49 mmol, 71%) as solid. $^1$H NMR (500 MHz, CDCl$_3$): δ 8.90 (s, 1H), 7.95 (dd, J=8.5, 2.5 Hz, 1H), 7.77 (d, J=8.0 Hz, 2H), 7.71 (d, J=8.0 Hz, 2H), 7.60 (d, J=8.5 Hz, 1H), 7.45-7.40 (m, 1H), 6.85 (app t, 1H), 6.75 (app t, 1H), 3.48 (d, J=5.0 Hz, 1H), 3.00 (app s, 1H). MS (ESI): m/z 428 [M$^+$+1].

To a stirred solution of coupled product (0.42 g, 0.98 mmol) in DMF (10 mL) was added K$_2$CO$_3$ (67 mg, 0.49 mmol) followed by 1H-tetrazole (68 mg, 0.98 mmol) at RT under an inert atmosphere. The reaction mixture was stirred for 5 h at 80° C. The volatiles were removed under reduced pressure and the obtained residue was dissolved in EtOAc (30 mL). The organic layer was washed with water and brine, was dried over anhydrous Na$_2$SO$_4$, and was concentrated under reduced pressure. The crude compound was purified by column chromatography to afford 2 (0.14 g, 0.28 mmol, 29%) as white solid. $^1$H NMR (500 MHz, CDCl$_3$): δ 8.76 (s, 1H), 8.73 (s, 1H), 8.01 (dd, J=8.0, 2.0 Hz, 1H), 7.78 (d, J=8.5 Hz, 2H), 7.72-7.67 (m, 3H), 7.49 (s, 1H), 7.44-7.37 (m, 1H), 6.81-6.76 (m, 1H), 6.71-6.65 (m, 1H), 5.57 (d, J=14.0 Hz, 1H), 5.19 (d, J=14.0 Hz, 1H). HPLC: 97.3%. MS (ESI): m/z 498 [M$^+$+1].

Chiral Preparative High-Performance Liquid Chromatography (HPLC) of Enantiomers:

The enantiomers of 2 (150 mg, 0.3 mmol) were separated by normal-phase preparative high performance liquid chromatography (Chiralpak IC, 250×21.2 mm, 5μ; using (A) n-hexane-(B) isopropyl alcohol (IPA) (A:B 60:40) as a mobile phase; flow rate: 11 mL/min) to obtain 2(+) (40 mg) and 2(−) (40 mg).

Analytical Data for 2 (+):

HPLC: 100%.

Chiral HPLC: R$_t$=22.7 min (Chiralpak IC, 250×4.6 mm, 5μ; mobile phase (A) n-Hexane-(B) IPA A:B 60:40; flow rate: 1.00 mL/min)

Optical rotation [α]$_D^{25}$: +18° (C=0.1% in methyl alcohol (MeOH)).

Example 3

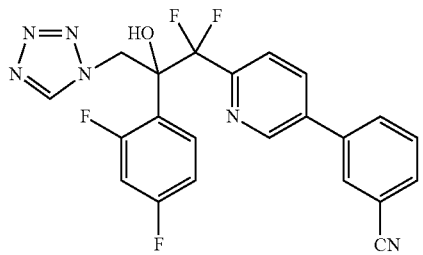 [SMILES: N#Cc1cccc(-c2ccc(C(F)(F)C(O)(Cn3cnnn3)c3ccc(F)cc3F)nc2)c1]

3-(6-(2-(2,4-Difluorophenyl)-1,1-difluoro-2-hydroxy-3-(1H-tetrazol-1-yl)propyl)pyridin-3-yl)benzonitrile (3)

Compound 3 was prepared using the conditions employed for 1. 0.020 g of 3 was isolated as a tan solid. $^1$H NMR (500 MHz, CDCl$_3$): δ 8.76 (s, 1H), 8.71 (s, 1H), 7.99 (dd, J=8.0, 2.0 Hz, 1H), 7.84 (s, 1H), 7.80-7.76 (m, 2H), 7.72 (d, J=8.0 Hz, 1H), 7.65 (t, J=7.5 Hz, 1H), 7.43-7.38 (m, 2H), 6.81-6.76 (m, 1H), 6.72-6.68 (m, 1H), 5.54 (d, J=14.5 Hz, 1H), 5.20 (d, J=14.5 Hz, 1H). HPLC: 93.95%. MS (ESI): m/z 455 [M$^+$+1].

Example 4

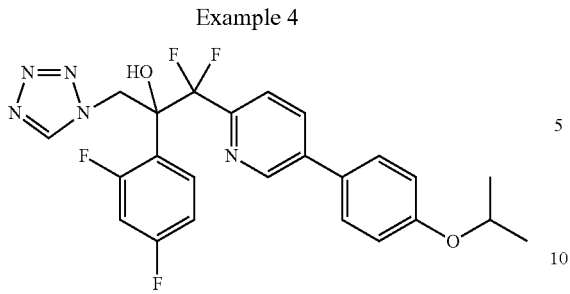

2-(2,4-Difluorophenyl)-1,1-difluoro-1-(5-(4-isopropoxyphenyl)pyridin-2-yl)-3-(1H-tetrazol-1-yl)propan-2-ol (4)

Compound 4 was prepared using the conditions employed for 1: 0.029 g of 4 was isolated as a white solid. $^1$H NMR (500 MHz, CDCl$_3$): δ 8.76 (s, 1H), 8.71 (s, 1H), 7.94 (dd, J=8.5, 2.5 Hz, 1H), 7.82 (s, 1H), 7.61 (d, J=8.0 Hz, 1H), 7.50-7.47 (m, 2H), 7.40-7.35 (m, 1H), 7.01-6.98 (m, 2H), 6.79-6.74 (m, 1H), 6.68-6.64 (m, 1H), 5.61 (d, J=14.0 Hz, 1H), 5.10 (d, J=14.0 Hz, 1H), 4.64-4.59 (m, 1H), 1.37 (d, J=6.0 Hz, 6H). HPLC: 99.1%. MS (ESI): m/z 488 [M$^+$+1].

Example 5

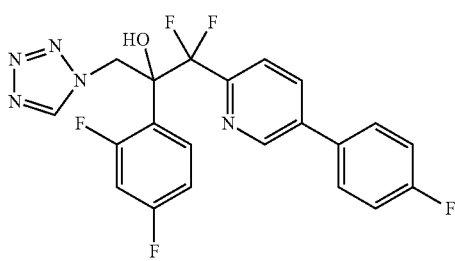 [SMILES: OC(Cn1cnnn1)(c1ccc(F)cc1F)C(F)(F)c1ccc(-c2ccc(F)cc2)cn1]

2-(2,4-Difluorophenyl)-1,1-difluoro-1-(5-(4-fluorophenyl)pyridin-2-yl)-3-(1H-tetrazol-1-yl)propan-2-ol (5)

Compound 5 was prepared using the conditions employed for 1: 0.033 g of 5 was isolated as a white solid. $^1$H NMR (500 MHz, CDCl$_3$): δ 8.76 (s, 1H), 8.69 (s, 1H), 7.95 (dd, J=8.0, 2.0 Hz, 1H), 7.66 (d, J=8.5 Hz, 2H), 7.55-7.52 (m, 2H), 7.42-7.37 (m, 1H), 7.22-7.19 (m, 2H), 6.80-6.75 (m, 1H), 6.70-6.66 (m, 1H), 5.58 (d, J=14.5 Hz, 1H), 5.15 (d, J=14.5 Hz, 1H). HPLC: 99.7%. MS (ESI): m/z 448 [M$^+$+1].

Example 6

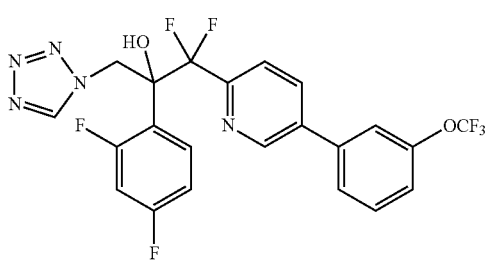 [SMILES: OC(Cn1cnnn1)(c1ccc(F)cc1F)C(F)(F)c1ccc(-c2cccc(OC(F)(F)F)c2)cn1]

2-(2,4-Difluorophenyl)-1,1-difluoro-3-(1H-tetrazol-1-yl)-1-(5-(3-(trifluoromethoxy)phenyl)-pyridin-2-yl)propan-2-ol (6)

Compound 6 was prepared using the conditions employed for 1: 0.028 g of 6 was isolated as a yellow solid. $^1$H NMR (500 MHz, CDCl$_3$): δ 8.76 (s, 1H), 8.73 (s, 1H), 7.98 (dd, J=8.0, 2.2 Hz, 1H), 7.69 (d, J=8.5 Hz, 1H), 7.57-7.49 (m, 3H), 7.41-7.33 (m, 3H), 6.80-6.75 (m, 1H), 6.70-6.66 (m, 1H), 5.59 (d, J=14.5 Hz, 1H), 5.16 (d, J=14.5 Hz, 1H). HPLC: 97.2%. MS (ESI): m/z 514 [M$^+$+1].

Example 7

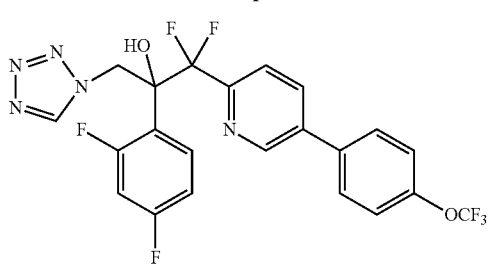

2-(2,4-Difluorophenyl)-1,1-difluoro-3-(1H-tetrazol-1-yl)-1-(5-(4-(trifluoromethoxy)phenyl)-pyridin-2-yl)propan-2-ol (7)

To a stirred solution of bromo epoxide C (0.5 g, 1.38 mmol) in THF (30 mL) and water (14 mL) were added 4-(trifluoromethoxy) phenylboronic acid (0.22 g, 1.1 mmol), Na$_2$CO$_3$ (0.32 g, 3.1 mmol) and Pd(dppf)$_2$Cl$_2$ (0.28 g, 0.34 mmol) at RT under an inert atmosphere. After purging with argon for a period of 30 min, the reaction mixture was heated to 75° C. and stirring was continued for 4 h. Progress of the reaction was monitored by TLC. The reaction mixture was cooled to RT and filtered through a pad of celite. The filtrate was concentrated under reduced pressure; the obtained residue was dissolved in EtOAc (30 mL). The organic layer was washed with water and brine, was dried over anhydrous Na$_2$SO$_4$ and was concentrated under reduced pressure. The crude compound was purified by column chromatography to afford the coupled product (0.45 g, 1.0 mmol, 73%) as solid. $^1$H NMR (200 MHz, CDCl$_3$): δ 8.87 (s, 1H), 7.90 (dd, J=8.2, 2.2 Hz, 1H), 7.66-7.54 (m, 3H), 7.49-7.34 (m, 3H), 6.90-6.70 (m, 2H), 3.49 (d, J=5.0 Hz, 1H), 3.02-2.95 (m, 1H). MS (ESI): m/z 444 [M$^+$+1].

To a stirred solution of the coupled product (0.45 g, 1.0 mmol) in DMF (10 mL) was added K$_2$CO$_3$ (70 mg, 0.5 mmol) followed by 1H-tetrazole (70 mg, 1.0 mmol) at RT under an inert atmosphere. The reaction mixture was stirred for 4 h at 80° C. The volatiles were removed under reduced pressure, and the obtained residue was dissolved in water (15 mL) and was extracted with EtOAc (2×20 mL). The combined organic layers were washed with water and brine and were dried over anhydrous Na$_2$SO$_4$ and concentrated under reduced pressure. The crude compound was purified by column chromatography to afford 7 (0.19 g, 0.37 mmol, 36%) as white solid. $^1$H NMR (500 MHz, CDCl$_3$): δ 8.76 (s, 1H), 8.70 (s, 1H), 7.97 (dd, J=8.0, 2.0 Hz, 1H), 7.68 (d, J=8.5 Hz, 1H), 7.60-7.56 (m, 3H), 7.43-7.36 (m, 3H), 6.80-6.76 (m, 1H), 6.70-6.67 (m, 1H), 5.57 (d, J=14.5 Hz, 1H), 5.17 (d, J=14.5 Hz, 1H). HPLC: 98.3%.

MS (ESI): m/z 513.9 [M$^+$+1].

Chiral Preparative HPLC of Enantiomers:

The enantiomers of 7 (17.8 g, 34.6 mmol) were separated by normal-phase preparative HPLC (Chiralpak AD-H, 250× 21.2 mm, 5μ; using (A) n-hexane-(B) IPA (A:B 70:30) as a mobile phase; flow rate: 15 mL/min) to obtain 7(+) (6.0 g) and 7(−) (5.8 g).

Analytical Data for 7 (+):

HPLC: 99.8%.

Chiral HPLC: $R_t$=9.88 min (Chiralpak AD-H, 250×4.6 mm, 5μ; mobile phase (A) n-Hexane-(B) IPA A:B 70:30; flow rate: 1.00 mL/min)

Optical rotation $[\alpha]_D^{25}$: +19° (C=0.1% in MeOH).

Example 8

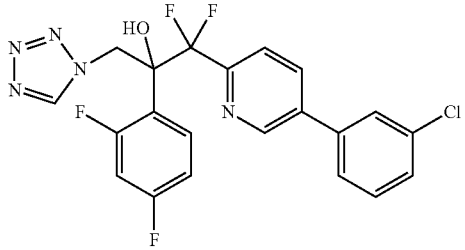 [SMILES: OC(Cn1cnnn1)(c1ccc(F)cc1F)C(F)(F)c1ccc(-c2cccc(Cl)c2)cn1]

1-(5-(3-Chlorophenyl)pyridin-2-yl)-2-(2,4-difluorophenyl)-1,1-difluoro-3-(1H-tetrazol-1-yl)propan-2-ol (8)

Compound 8 was prepared using the conditions employed for 1: 0.028 g of 8 was isolated as a white solid. $^1$H NMR (500 MHz, CDCl$_3$): δ 8.76 (s, 1H), 8.72 (s, 1H), 7.97 (dd, J=8.5, 2.2 Hz, 1H), 7.67 (d, J=8.0 Hz, 1H), 7.56-7.54 (m, 2H), 7.46-7.43 (m, 3H), 7.40-7.35 (m, 1H), 6.80-6.75 (m, 1H), 6.70-6.66 (m, 1H), 5.59 (d, J=14.5 Hz, 1H), 5.16 (d, J=14.5 Hz, 1H). HPLC: 98.79%. MS (ESI): m/z 463.9 [M$^+$].

Example 9

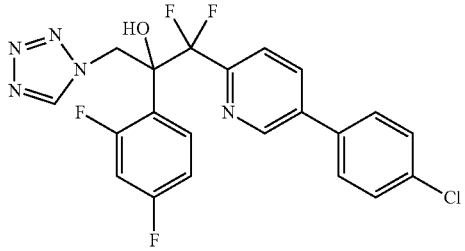 [SMILES: OC(Cn1cnnn1)(c1ccc(F)cc1F)C(F)(F)c1ccc(-c2ccc(Cl)cc2)cn1]

1-(5-(4-Chlorophenyl)pyridin-2-yl)-2-(2,4-difluorophenyl)-1,1-difluoro-3-(1H-tetrazol-1-yl)propan-2-ol (9)

Compound 9 was prepared using the conditions employed for 1: 0.027 g of 9 was isolated as a white solid. $^1$H NMR (500 MHz, CDCl$_3$): δ 8.75 (s, 1H), 8.70 (s, 1H), 7.96 (d, J=8.5 Hz, 1H), 7.66 (d, J=8.5 Hz, 1H), 7.60 (s, 1H), 7.49 (s, 4H), 7.42-7.37 (m, 1H), 6.79-6.76 (m, 1H), 6.70-6.67 (m, 1H), 5.58 (d, J=14.5 Hz, 1H), 5.16 (d, J=14.5 Hz, 1H). HPLC: 99.07%. MS (ESI): m/z 463.9 [M$^+$].

Chiral Preparative HPLC of Enantiomers:

The enantiomers of 9 (200 mg, 0.4 mmol) were separated by normal-phase preparative HPLC (Chiralpak IC, 250×21.1 mm, 5μ; using (A) n-hexane-(B) ethyl alcohol (A:B 75:25) as a mobile phase; flow rate: 15 mL/min) to obtain 9(+) (62 mg) and 9(−) (55 mg).

Analytical Data for 9 (+):
HPLC: 100%
Chiral HPLC: $R_t$=15.3 min (Chiralpak IC, 250×4.6 mm, 5μ; mobile phase (A) n-Hexane-(B) ethyl alcohol A:B 75:25; flow rate: 1.00 mL/min)
Optical rotation $[\alpha]_D^{25}$: +26.5° (C=0.1% in MeOH).

Example 10

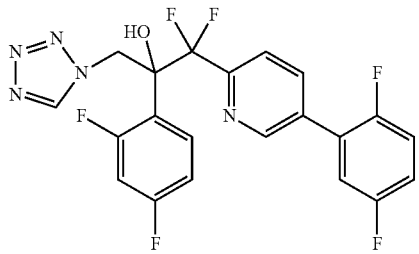 [SMILES: OC(Cn1cnnn1)(c1ccc(F)cc1F)C(F)(F)c1ccc(-c2cc(F)ccc2F)cn1]

2-(2,4-Difluorophenyl)-1-(5-(2,5-difluorophenyl)pyridin-2-yl)-1,1-difluoro-3-(1H-tetrazol-1-yl)propan-2-ol (10)

Compound 10 was prepared using the conditions employed for 1: 0.022 g of 10 was isolated as a yellow solid. $^1$H NMR (500 MHz, CDCl$_3$): δ 8.76 (s, 1H), 8.70 (s, 1H), 7.98 (d, J=8.0 Hz, 1H), 7.69 (d, J=8.0 Hz, 1H), 7.49 (s, 1H), 7.41-7.36 (m, 1H), 7.20-7.11 (m, 3H), 6.79-6.75 (m, 1H), 6.70-6.67 (m, 1H), 5.60 (d, J=14.5 Hz, 1H), 5.16 (d, J=14.5 Hz, 1H). HPLC: 98.68%. MS (ESI): m/z 466 [M$^+$].

Example 11

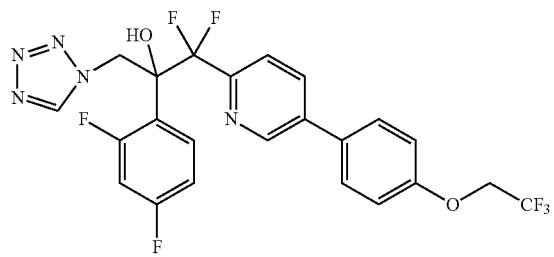 [SMILES: OC(Cn1cnnn1)(c1ccc(F)cc1F)C(F)(F)c1ccc(-c2ccc(OCC(F)(F)F)cc2)cn1]

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11)

Compound 11 was prepared using the conditions employed for 1: 0.33 g of 11 was isolated as a solid. The precursor 1-bromo-4-(2,2,2-trifluoroethoxy)benzene was prepared as described below in one step.

$^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.44-4.39 (m, 2H). HPLC: 99.1%. MS (ESI): m/z 528 [M$^+$+1].

Chiral Preparative HPLC of Enantiomers:

The enantiomers of 11 (330 mg, 0.626 mmol) were separated by normal-phase preparative HPLC (Chiralpak IC, 250×21.1 mm, 5μ; using (A) n-hexane-(B) IPA (A:B 65:35) as a mobile phase; Flow rate: 15 mL/min) to obtain 11(+) (126.3 mg) and 11(−) (112.7 mg).

Analytical Data for 11 (+):
HPLC: 99.8%
Chiral HPLC: $R_t$=13.40 min (Chiralpak IA, 250×4.6 mm, 5μ; mobile phase (A) n-Hexane-(B) IPA A:B 65:35; flow rate: 1.00 mL/min)
Optical rotation $[\alpha]_D$: +24° (C=0.1% in MeOH).

1-Bromo-4-(2,2,2-trifluoroethoxy)benzene

To a stirred solution of trifluoroethyl tosylate (1.5 g, 5.8 mmol) in DMF (20 mL) was added $K_2CO_3$ (4 g, 29.4 mmol) followed by p-bromo phenol (1.1 g, 6.46 mmol) at RT under an inert atmosphere. The reaction mixture was stirred at 120° C. for 6 h. The volatiles were evaporated under reduced pressure; the residue was diluted with water (5 mL) and extracted with EtOAc (3×30 mL). The organic layer was washed with water and brine, was dried over anhydrous $Na_2SO_4$, was filtered and was concentrated in vacuo. The crude compound was purified by silica gel column chromatography eluting with 5% EtOAc/hexane to afford the desired product (0.8 g, 3.13 mmol, 53.3%) as semi solid. $^1$H NMR (200 MHz, $CDCl_3$): δ 7.44-7.38 (m, 2H), 6.86-6.80 (m, 2H), 4.38-4.25 (m, 2H).

Example 12

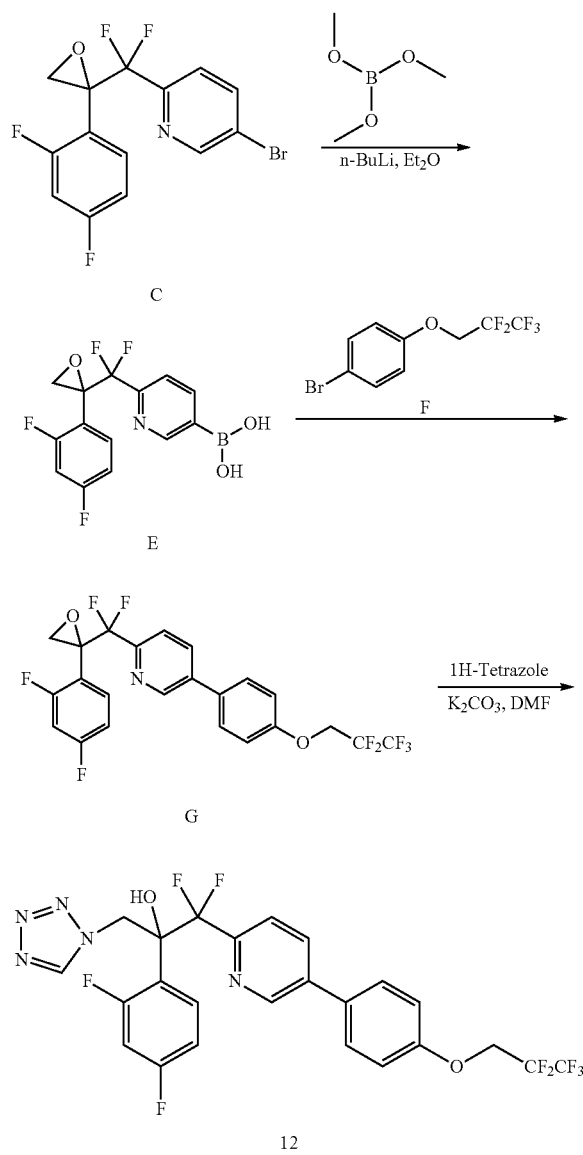

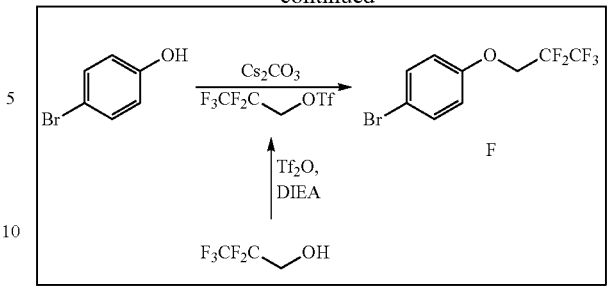

2-(2,4-Difluorophenyl)-1,1-difluoro-1-(5-(4-(2,2,3,3,3-pentafluoropropoxy)phenyl)pyridin-2-yl)-3-(1H-tetrazol-1-yl)propan-2-ol (12)

To a stirred solution of trifluorethanol (10 g, 0.06 moles (mol)) in dry $CH_2Cl_2$ (100 mL) was added N,N-diisopropylethylamine (DIPEA; 29 mL, 0.16 mol) at RT, and the reaction mixture was cooled to −78° C. Triflic anhydride (13.5 mL, 0.07 mol) was added dropwise to the reaction mixture at −78° C. After being stirred for 30 min, the reaction mixture was warmed to −30° C. and stirring was continued for another 30 min. The reaction mixture was quenched with water (200 mL) and extracted with $CH_2Cl_2$ (2×300 mL). The combined organic layers were washed with 1 N hydrochloric acid (HCl) and water, dried over anhydrous $Na_2SO_4$, and filtered. To a stirred solution of 4-bromophenol (4 g, 0.02 mol) and cesium carbonate ($Cs_2CO_3$; 15 g, 0.04 mol) in DMF (100 mL) was added the $CH_2Cl_2$ layer from above (H) at RT. The mixture was stirred for 16 h. The progress of the reaction was monitored by TLC. The reaction mixture was diluted with water and was extracted with $CH_2Cl_2$ (2×250 mL). The combined organic layers were dried over anhydrous $Na_2SO_4$, filtered and concentrated under reduced pressure. The obtained crude material was purified by column chromatography ($SiO_2$, 60-120 mesh) to afford compound F (3.5 g, 11.5 mmol, 50%) as a liquid. $^1$H NMR (200 MHz, $CDCl_3$): δ 7.46-7.38 (m, 2H), 6.87-6.79 (m, 2H), 4.45-4.32 (m, 2H). To a stirred solution of n-BuLi (21 mL, 33.13 mmol, 1.5 M in hexane) in dry ether (250 mL) was added a solution of compound C (8 g, 22.09 mmol) in ether (50 mL) at −78° C. After being stirred for 30 min, trimethyl borate (5 mL, 44.19 mmol) was added to the reaction mixture at −78° C., and the stirring was continued for another 10 min. The reaction mixture was allowed to warm to room temperature and was stirred for 30 min. The reaction mixture was quenched with acetic acid (40 mL), was diluted with water (120 mL) and was stirred for 1 h at RT. The reaction mixture was brought to pH~12 by the addition of 2 N sodium hydroxide (NaOH), the organic layer was separated and the aqueous layer was brought to pH~6 using 1 N HCl. The aqueous layer was extracted with $CH_2Cl_2$ (2×500 mL). The combined organic layers were dried over anhydrous $Na_2SO_4$ and concentrated under reduced pressure to afford compound E (7 g, 21.4 mmol, 97%) as a brown white solid. $^1$H NMR (500 MHz, $CD_3OD$): δ 8.81 (s, 1 H), 8.15 (d, J=7.5 Hz, 1 H), 7.47 (d, J=8 Hz, 1 H), 7.36-7.35 (m, 1 H), 6.93-6.87 (m, 2 H), 3.42 (d, J=5.5 Hz, 1 H), 2.99-2.98 (m, 1 H). MS (ESI): m/z 328.1 [M$^+$+1].

A mixture of boronic acid E (3.5 g, 10.7 mmol), compound F (3.3 g, 10.7 mol) and $K_2CO_3$ (4.5 g, 32.1 mmol) in THF/$H_2O$ (175 mL, 4: 1) was degassed for 30 min. Pd (dppf)$_2$ Cl$_2$ (0.7 g, 1.07 mmol) was added to the reaction mixture under an inert atmosphere, and the resulting mixture was stirred at 70° C. for 2 h. The reaction mixture was allowed to cool to room temperature and the volatiles were removed under reduced pressure. The obtained crude material was purified by column chromatography (SiO$_2$, 60-120 mesh; eluent: 15-55% EtOAc/hexanes) to afford compound G (2.3 g, 4.53 mmol, 43%) as an off-white solid. $^1$H NMR (200 MHz, CDCl$_3$): δ 8.83 (d, J=2.2 Hz, 1H), 7.90 (dd, J=2.2, 8.0 Hz, 1H), 7.61-7.48 (m, 3H), 7.43-7.36 (m, 1H), 7.29 (d, J=8.8 Hz, 2H), 7.10-7.04 (m, 2H), 6.89-6.70 (m, 2H), 4.48 (q, J=12.4 Hz, 2H), 3.45 (d, J=5.0 Hz, 1H), 3.01-2.98 (m, 1H).

To a stirred solution of compound G (10.5 g, 20.7 mmol) in DMF (150 mL) was added $K_2CO_3$ (3.4 g, 20.7 mmol) followed by 1H-tetrazole (2.6 g, 37.1 mmol) at RT. The reaction mixture was heated to 70° C. for 16 h. Progress of the reaction was monitored by TLC. The reaction mixture was allowed to cool to room temperature and diluted with water (300 mL). The aqueous layer was extracted with EtOAc (3×300 mL). The combined organic layer was dried over anhydrous $Na_2SO_4$ and concentrated in vacuo. The crude compound was purified by column chromatography (SiO$_2$, 60-120 mesh; eluent: 15-55% EtOAc/hexanes) to afford 12 (6 g, 10.38 mmol, 50.4%) as a white solid. $^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.48 (t, J=12.0 Hz, 2H). MS (ESI): m/z 578.1 [M$^+$+1].

Chiral preparative HPLC of Enantiomers:

The enantiomers of 12 (6 g, 10.3 mmol) were separated by normal-phase preparative HPLC (Chiralpak IA, 250×21.2 mm, 5μ; using (A) n-hexane-(B) ethyl alcohol (A:B 80:20) as a mobile phase; flow rate: 12 mL/min) to obtain 12(+) (2.1 g) and 12(−) (2.0 g).

Analytical Data for 12 (+):

$^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.48 (t, J=12.0 Hz, 2H). HPLC: 98.1%. MS (ESI): m/z 578.1 [M$^+$+1].

Chiral HPLC: R$_t$=14.12 min (Chiralpak IA, 250×4.6 mm, 5μ; mobile phase (A) n-Hexane-(B) ethanol A:B 80:20; flow rate: 1.00 mL/min).

Optical rotation [α]$_D^{25}$: +22.3° (C=0.1% w/v in MeOH).

Example 13

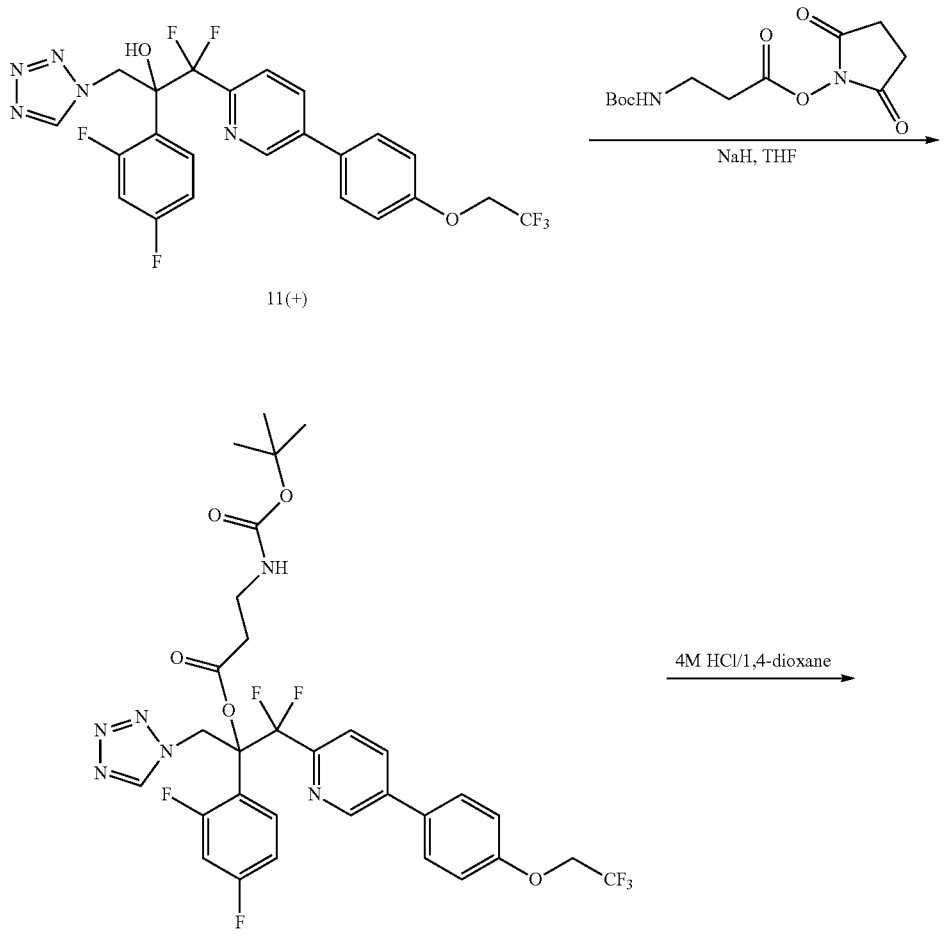

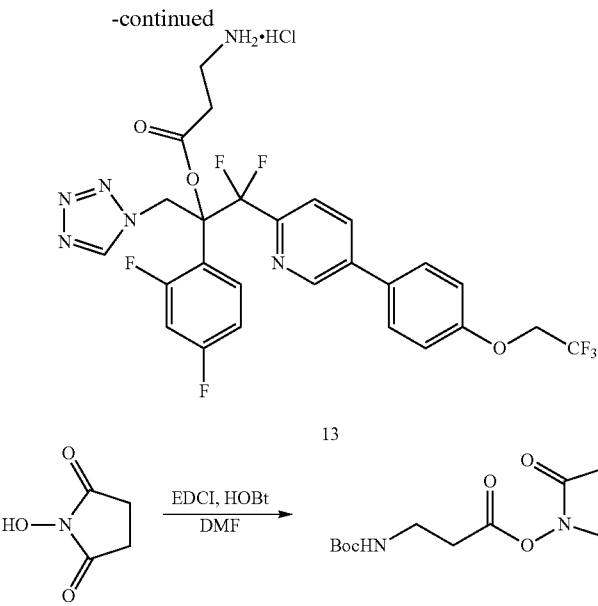

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate hydrochloride (13)

To mixture of Boc-β-alanine (N-Boc-β-Ala-OH; 1 g, 5.29 mmol) and N-hydroxysuccinimide (0.9 g, 7.82 mmol) in DMF (10 mL) were added 1-hydroxybenzotriazole hydrate (HOBt.xH$_2$O; 0.7 g, 5.25 mmol) and 1-ethyl-3-(3-dimethylaminopropyl)carbodiimide hydrochloride (EDCI.HCl; 1 g, 5.23 mmol) at 5° C. The reaction mixture was warmed to RT and stirred for 16 h. The progress of the reaction was monitored by TLC. The reaction was quenched with water and the mixture was extracted with EtOAc (2×150 mL). The combined organic layers were washed with water (3×100 mL) and brine (150 mL), dried over anhydrous Na$_2$SO$_4$ and concentrated under reduced pressure. The crude compound was triturated with ether (2×25 mL) to afford N-Boc-β-Ala-OSu (1.1 g, crude) as a white solid. $^1$H NMR (500 MHz, CDCl$_3$): δ 5.10 (br s, 1H), 3.52 (q, J=6.0 Hz, 2H), 2.85-2.82 (m, 6H), 1.31 (s, 9H).

To a suspension of 11-(+) (0.2 g, 0.38 mmol) in dry THF (20 mL) was added sodium hydride (NaH; 0.02 g, 1.17 mmol) at 0° C., and the mixture was stirred for 30 min at RT. N-Boc-β-Ala-OSu (0.21 g, 0.70 mmol) was added to the reaction mixture and the stirring was continued for another 16 h at RT. The progress of the reaction was monitored by TLC. The reaction mixture was quenched with ice cold water and was extracted with EtOAc (2×50 mL). The combined organic layers were dried over anhydrous Na$_2$SO$_4$ and concentrated under reduced pressure to afford crude product, which upon separation by preparative TLC (SiO$_2$, 60-120 mesh; eluent: 15-55% EtOAc/hexanes) afforded compound I (38 mg, 0.06 mmol, 15%). $^1$H NMR (500 MHz, CDCl$_3$): δ 9.27 (s, 1H), 8.92 (s, 1H), 7.80 (dd, J=1.5, 8.0 Hz, 1H), 7.58 (d, J=8.5 Hz, 2H), 7.14-7.13 (m, 1H), 7.09 (d, J=8.5 Hz, 2H), 7.04 (d, J=8.0 Hz, 1H), 6.89 (t, J=7.0 Hz, 1H), 6.71-6.66 (m, 1H), 6.09 (dd, J=2.5, 15.0 Hz, 1H), 5.73 (dd, J=2.5, 15.0 Hz, 1H), 5.23 (br s, 1H), 4.45-4.40 (m, 2H), 3.46 (br s, 2H), 2.82-2.69 (m, 2H), 1.28 (s, 9H). MS (ESI): m/z 699.3 [M$^+$+1].

To a stirred solution of compound I (0.03 g, 0.05 mmol) in 1,4-dioxane (2 mL) was added 4 M HCl solution in 1,4-dioxane (1 mL) at 5° C., and the mixture was stirred for 4 h at RT. The progress of the reaction was monitored by TLC. The volatiles were evaporated under reduced pressure. The obtained crude was triturated with diethyl ether (2×25 mL) to afford 13 (0.018 g, 0.02 mmol, 55%) as a white solid. $^1$H NMR (500 MHz, DMSO-d$_6$): δ 9.67 (s, 1H), 9.04 (s, 1H), 8.13 (dd, J=1.5, 8.0 Hz, 1H), 7.88 (s, 2H), 7.78 (d, J=8.5 Hz, 2H), 7.38-7.36 (m, 1H), 7.27-7.24 (m, 1H), 7.24 (d, J=8.0 Hz, 1H), 7.17 (d, J=8.0 Hz, 1H), 6.15 (d, J=15.5 Hz, 1H), 5.54 (d, J=15.5 Hz, 1H), 4.87 (q, J=8.5 Hz, 2H), 3.06 (d, J=5.5 Hz, 2H), 2.93-2.83 (m, 2H). HPLC: 93.64%. MS (ESI): m/z 599.4 [M$^+$+1].

Example 14

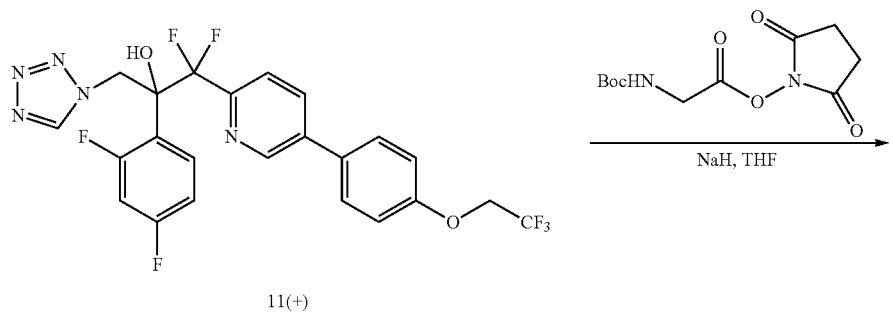

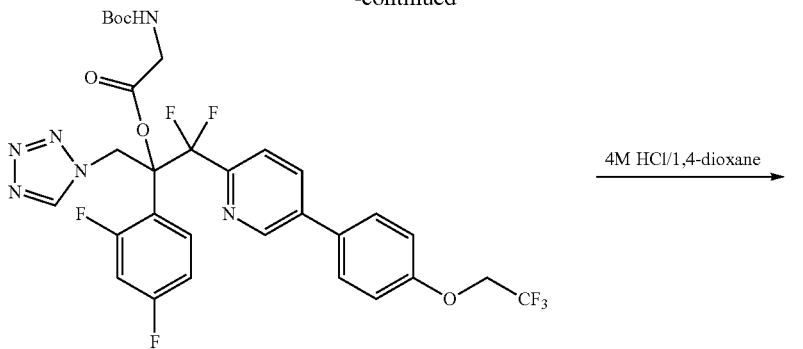

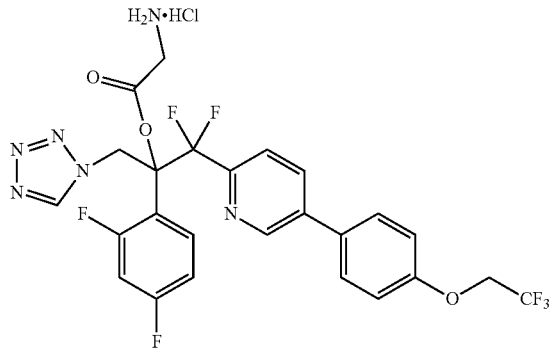

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14)

To a suspension of 11-(+) (0.1 g, 0.18 mmol) in dry THF (30 mL) was added NaH (0.01 g, 0.41 mmol) at 5° C. and the mixture was stirred for 40 min at RT. Boc-Glycine N-hydroxysuccinimide ester (N-Boc-Gly-OSu; 0.1 g, 0.37 mmol) was added to the reaction mixture, and the stirring was continued for another 16 h at RT. The progress of the reaction was monitored by TLC. The reaction was quenched with ice cold water and extracted with EtOAc (2×50 mL). The combined organic layers were dried over anhydrous $Na_2SO_4$ and concentrated under reduced pressure to afford crude product, which upon separation by preparative TLC ($SiO_2$, 60-120 mesh; eluent: 15-55% EtOAc/hexanes) afforded compound J (29 mg, 0.04 mmol, 24%). $^1$H NMR (500 MHz, DMSO-$d_6$): δ9.34 (s, 1H), 8.92 (s, 1H), 7.80 (d, J=7.0 Hz, 1H), 7.59-7.54 (m, 2H), 7.44-7.42 (m, 1H), 7.10-7.03 (m, 3H), 6.94-6.91 (m, 1H), 6.64 (t, J=10.0 Hz, 1H), 6.12 (dd, J=2.5, 15.0 Hz, 1H), 5.69 (dd, J=3.5, 15.0 Hz, 1H), 5.10 (d, J=6.0 Hz, 1H), 4.43 (q, J=8.5 Hz, 2H), 4.21-4.16 (m, 1H), 3.95 (dd, J=5.0, 18.0 Hz, 1H), 1.45 (s, 9H). MS (ESI): m/z 685.3 [M$^+$+1].

To a stirred solution of compound J (0.02 g, 0.04 mmol) in 1,4-dioxane (2 mL) was added a 4 M HCl solution in 1,4-dioxane (1 mL) dropwise at 5° C. The reaction mixture was stirred for 4 h at RT. The progress of the reaction was monitored by TLC. The volatiles were evaporated under reduced pressure. The obtained crude product was triturated with diethyl ether (3×25 mL) to afford 14 (14 mg, 0.02 mmol, 60%) as a white solid. $^1$H NMR (500 MHz, DMSO-$d_6$): δ 9.68 (s, 1H), 9.04 (s, 1H), 8.45-8.43 (m, 2H), 8.14 (d, J=8.5 Hz, 2H), 7.79 (d, J=9.0 Hz, 2H), 7.45-7.44 (m, 1H), 7.29-7.27 (m, 1H), 7.24-7.23 (m, 3H), 7.14-7.10 (m, 1H), 6.18 (d, J=16.0 Hz, 1H), 5.57 (d, J=15.0 Hz, 1H), 4.87 (q, J=8.5 Hz, 2H), 4.16 (d, J=18.0 Hz, 1H), 3.94 (d, J=18.5 Hz, 1H). HPLC: 93.54%. MS (ESI): m/z 585 [M$^+$+1].

Example 15

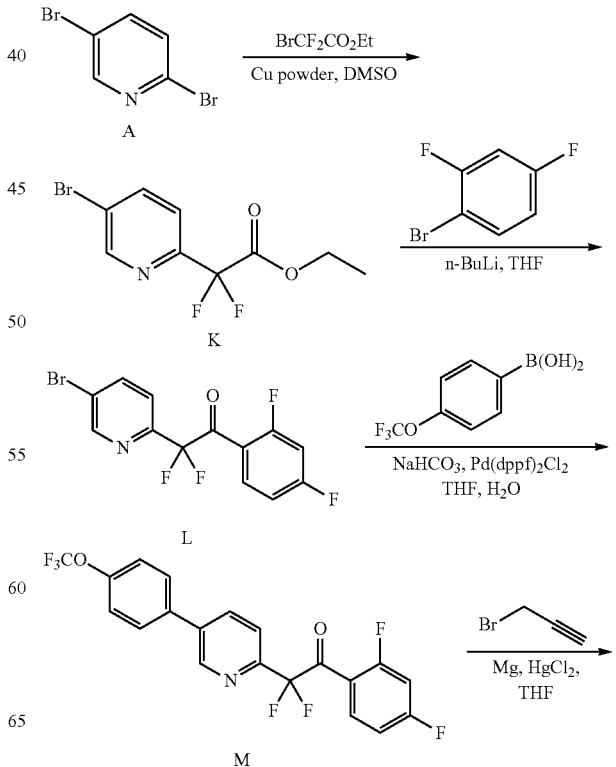

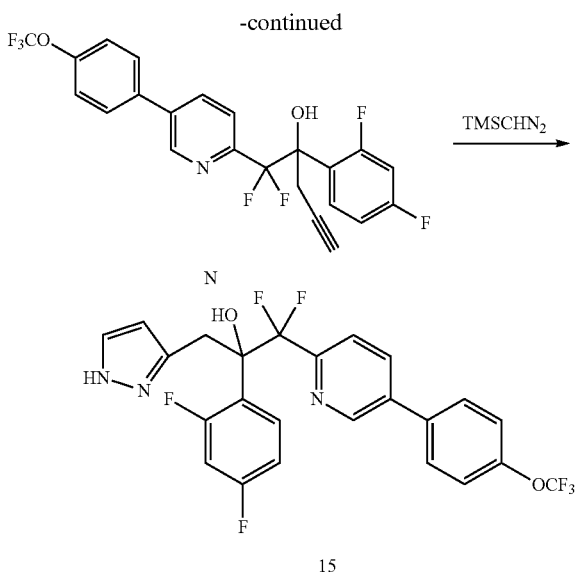

2-(2,4-Difluorophenyl)-1,1-difluoro-3-(1H-pyrazol-3-yl)-1-(5-(4-(trifluoromethoxy)phenyl)-pyridin-2-yl)propan-2-ol (15)

To a suspension of copper powder (27 g, 0.42 mol) in DMSO (300 mL) was added ethyl α-bromo-difluoroacetate (27 mL, 0.21 mol) and the mixture was stirred for 1 h at RT. 2,5-Dibromopyridine (25 g, 0.10 mol) was then added and stirring was continued for another 15 h at RT. The progress of the reaction was monitored by TLC. The reaction was quenched with saturated $NH_4Cl$ solution (200 mL) and extracted with $CH_2Cl_2$ (3×250 mL). The combined organic layers were washed with water and brine, dried over anhydrous $Na_2SO_4$ and concentrated under reduced pressure to afford crude product, which upon distillation under reduced pressure afforded compound K (19 g, 67.8 mmol, 64%) as a pale yellow oil. $^1$H NMR (500 MHz, $CDCl_3$): δ 8.71 (s, 1H), 8.00 (d, J=9.0 Hz, 1H), 7.62 (d, J=9.0 Hz, 1H), 4.42-4.35 (m, 2H), 1.39-1.31 (m, 3H).

To a stirred solution of 1-bromo-2,4-difluorobenzene (7.6 mL, 67.8 mmol) in diethyl ether (100 mL) was added n-BuLi (42 mL, 67.85 mmol, 1.6 M in hexane) at −78° C. After being stirred for 45 min at −78° C., a solution of ester K (19 g, 67.8 mmol) in diethyl ether (100 mL) was added to the reaction mixture and the stirring was continued for another 1 h at −78° C. under an inert atmosphere. The reaction mixture was warmed to RT and was stirred for another 3 h. The progress of the reaction was monitored by TLC. The reaction was quenched with saturated $NH_4Cl$ solution (200 mL) and the reaction mixture was extracted with EtOAc (3×200 mL). The combined organic layers were washed with water and brine, dried over anhydrous $Na_2SO_4$ and concentrated under reduced pressure. The crude compound was purified by column chromatography ($SiO_2$, 100-200 mesh) eluting with 2% EtOAc/hexane to afford ketone L (13 g, 37.3 mmol, 55%) as yellow liquid. $^1$H NMR (500 MHz, $CDCl_3$): δ 8.62 (s, 1H), 8.08-8.04 (m, 2H), 7.72 (d, J=8.5 Hz, 1H), 7.05-6.95 (m, 1H), 6.88-6.78 (m, 1H). MS (ESI): m/z 347[M$^+$+1], 349 [(M$^+$+2].

To a stirred solution of ketone L (1.0 g, 2.87 mmol) in THF (30 mL) and water (10 mL) were added (4-(trifluoromethoxy)phenyl)boronic acid (591 mg, 2.87 mmol), sodium bicarbonate ($NaHCO_3$; 782 mg, 7.18 mmol) and $Pd(dppf)_2Cl_2$ (586 mg, 0.718 mmol) at RT under an inert atmosphere. After purging with argon for a period of 30 min, the reaction mixture was heated to 65° C. and stirring was continued for 2 h. Progress of the reaction was monitored by TLC. The reaction mixture was cooled to RT and filtered through a pad of celite. The filtrate was concentrated under reduced pressure, and the obtained residue was dissolved in EtOAc (2×50 mL). The organic layer was washed with water and brine, dried over anhydrous $Na_2SO_4$ and concentrated under reduced pressure. The crude compound was purified by column chromatography ($SiO_2$, 100-200 mesh; eluent: 15-55% EtOAc/hexanes) to afford M (980 mg, 2.28 mmol, 79%) as light yellow sticky solid. $^1$H NMR (200 MHz, $CDCl_3$): δ 8.77 (s, 1H), 8.12-8.03 (m, 2H), 7.90 (d, J=8.4 Hz, 1H), 7.63-7.57 (m, 2H), 7.35 (d, J=8.2 Hz, 2H), 7.05-6.96 (m, 1H), 6.83-6.79 (m, 1H). MS (ESI): m/z 430 [M$^+$+1].

To a mixture of magnesium (Mg; 50 mg, 2.08 mmol) and mercuric chloride ($HgCl_2$; 47 mg, 0.17 mmol) in dry THF (5 mL) was added propargyl bromide (0.05 mL, 0.34 mmol) at RT under an inert atmosphere, and the mixture was stirred for 20 min. The reaction mixture was then cooled to −20° C., and ketone M (150 mg, 0.348 mmol) and the remaining portion of propargyl bromide (0.05 mL, 0.34 mmol) in THF (5 mL) were added. Stirring was continued for 2 h at −20° C. The progress of the reaction was monitored by TLC. The reaction was quenched with a saturated $NH_4Cl$ solution and the reaction mixture was extracted with $CH_2Cl_2$ (3×50 mL). The combined organic layers were washed with water and brine, dried over anhydrous $Na_2SO_4$ and concentrated in vacuo. The crude product was purified by column chromatography ($SiO_2$, 100-200 mesh; eluent: 15-55% EtOAc/hexanes) to afford N (110 mg, 0.23 mmol, 67%) as a solid. $^1$H NMR (200 MHz, $CDCl_3$): δ 8.86 (s, 1H), 7.96 (dd, J=8.4, 2.2 Hz, 1H), 7.65-7.57 (m, 4H), 7.41 (d, J=8.2 Hz, 2H), 6.88-6.73 (m, 2H), 6.36 (br s, 1H), 3.46 (dd, J=16.8, 2.2 Hz, 1H), 2.98 (dt, J=16.8, 2.6 Hz, 1H), 1.85 (t, J=2.6 Hz, 1H). MS (ESI): m/z 470 [M$^+$+1].

A solution of N (110 mg, 0.23 mmol) in TMSCHN$_2$ (1 mL, 1.15 mmol) was stirred at 120° C. for 15 h. The volatiles were evaporated under reduced pressure and the obtained crude material was purified by column chromatography ($SiO_2$, 100-200 mesh; eluent: 15-55% EtOAc/hexanes) to afford 15 (35 mg, 0.06 mmol, 29%) as an off-white solid. $^1$H NMR (500 MHz, $CDCl_3$): δ 8.80 (s, 1H), 7.93 (d, J=8.5 Hz, 1H), 7.62-7.59 (m, 3H), 7.50-7.45 (m, 1H), 7.36-7.31 (m, 3H), 6.83 (br s, 1H), 6.70-6.65 (m, 2H), 6.04 (s, 1H), 4.02 (d, J=15.0 Hz, 1H), 3.36 (d, J=15.0 Hz, 1H). MS (ESI): m/z 512 [M$^+$+1]. HPLC: 95.6%.

Example 16

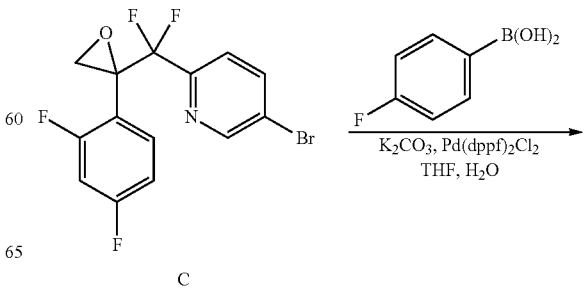

Example 17

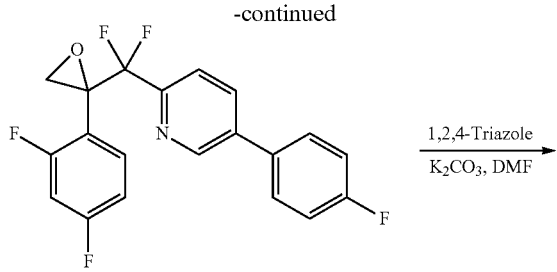

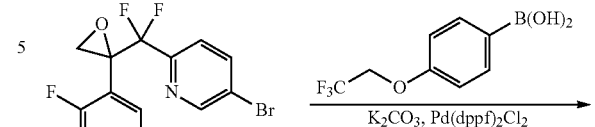

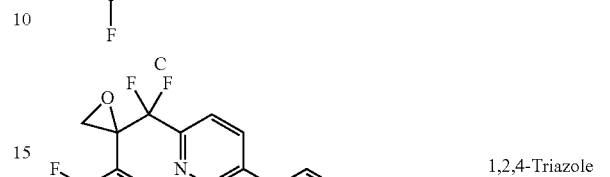

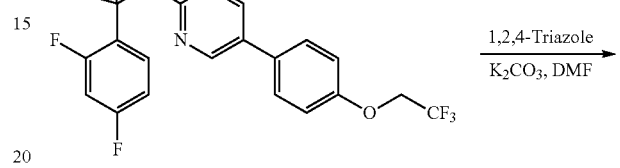

2-(2,4-Difluorophenyl)-1,1-difluoro-1-(5-(4-fluorophenyl)pyridin-2-yl)-3-(1H-1,2,4-triazol-1-yl)propan-2-ol (16)

To a stirred solution of 5-bromo-2-((2-(2,4-difluorophenyl)oxiran-2-yl)difluoromethyl)pyridine (C; 1.0 g, 2.7 mmol) in THF:H$_2$O (20 mL, 4:1 mixture) was added (4-fluorophenyl)boronic acid (378 mg, 2.7 mmol) followed by K$_2$CO$_3$ (1.1 g, 8.1 mmol) at RT, and the mixture was degassed by purging with inert gas for 45 min. To the resulting reaction mixture was added Pd(dppf)$_2$Cl$_2$ (197 mg, 0.27 mmol), and the reaction mixture was further degassed for 20 min at RT. The reaction mixture was then heated to 60° C. and stirred for 4 h. After complete consumption of the starting material (by TLC), the reaction mixture was cooled to RT, diluted with water and the organic layer separated. The aqueous layer with extracted with EtOAc (2×20 mL). The combined organic extracts were dried over anhydrous Na$_2$SO$_4$ and concentrated under reduced pressure to obtain the crude material. The crude material was purified by silica gel column chromatography (eluent: 20% EtOAc/hexane) to afford O (0.9 g, 2.38 mmol, 86%) as colorless semi-solid. $^1$H NMR (200 MHz, CDCl$_3$): δ 8.85 (d, J=2.0 Hz, 1H), 7.89 (dd, J=8.2, 2.4 Hz, 1H), 7.62-7.36 (m, 4H), 7.24-7.19 (m, 2H), 6.90-6.70 (m, 2H), 3.48 (d, J=4.8 Hz, 1H), 3.02-2.98 (m, 1H).

To a stirred solution of compound O (0.3 g, 0.79 mmol) in DMF (3 mL) was added K$_2$CO$_3$ (109 mg, 0.79 mmol) followed by 1,2,4-triazole (81 mg, 1.18 mmol) at RT under an inert atmosphere. The reaction mixture was then heated to 60° C. and stirred for 16 h. After complete consumption of the starting material (by TLC), the reaction mixture was diluted with water and extracted with EtOAc (3×15 mL). The combined organic extracts were dried over anhydrous Na$_2$SO$_4$ and concentrated under reduced pressure to obtain the crude product. The crude material was purified by silica gel column chromatography (eluent: 40% EtOAc/hexane) to afford 16 (250 mg, 0.56 mmol, 72.6%) as an off-white solid. $^1$H NMR (500 MHz, CDCl$_3$): δ 8.72 (s, 1H), 8.16 (s, 1H), 7.92 (d, J=8.5 Hz, 1H), 7.69 (s, 1H), 7.62 (d, J=8.5 Hz, 1H), 7.56-7.47 (m, 3H), 7.22-7.18 (m, 2H), 6.77-6.71 (m, 3H), 5.38 (d, J=14.0 Hz, 1H), 4.90 (d, J=14.0 Hz, 1H). MS (ESI): m/z 447 [M$^+$+1]. HPLC: 98.36%.

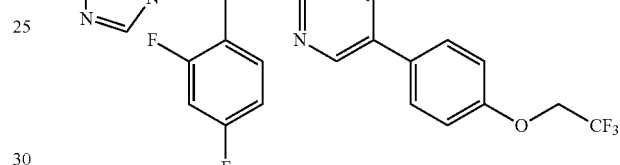

2-(2,4-Difluorophenyl)-1,1-difluoro-3-(1H-1,2,4-triazol-1-yl)-1-(5-(4-(2,2,2-trifluoroethoxy)phenyl)pyridin-2-yl)propan-2-ol (17)

To a stirred solution of epoxy bromide C (190 mg, 0.52 mmol) in THF:H$_2$O (40 mL, 4:1 mixture) was added (4-(2,2,2-trifluoroethoxy)phenyl)boronic acid (174 mg, 0.57 mmol) followed by K$_2$CO$_3$ (215 mg, 1.56 mmol) at RT, and the mixture was degassed by purging with inert gas for 30 min. To the resulting reaction mixture was added Pd(dppf)$_2$Cl$_2$ (20 mg, 0.027 mmol), and the mixture was further degassed for 20 min at RT. The reaction mixture was then heated to 70° C. and stirred for 2 h. Progress of the reaction was monitored by TLC.

The reaction mixture was cooled to RT, diluted with EtOAc (20 mL) and filtered through a celite pad. The collected filtrate was washed with water (2×50 mL). The separated organic layer was dried over anhydrous Na$_2$SO$_4$ and concentrated under reduced pressure to obtain the crude product. The crude material was purified by silica gel column chromatography (eluent: 15% EtOAc/hexane) to afford P (0.2 g, 0.43 mmol, 84%) as an off-white solid. $^1$H NMR (200 MHz, CDCl$_3$): δ 8.85 (d, J=2.2 Hz, 1H), 7.89 (dd, J=8.2, 2.2 Hz, 1H), 7.59-7.51 (m, 3H), 7.48-7.36 (m, 1H), 7.08 (dd, J=7.0, 2.2 Hz, 2H), 6.89-6.70 (m, 2H), 4.42 (q, J=8.2 Hz, 2H), 3.48 (d, J=5.0 Hz, 1H), 3.01-2.98 (m, 1H). MS (ESI): m/z 458 [M$^+$+1].

To a stirred solution of compound P (0.2 g, 0.43 mmol) in DMF (20 mL) was added K$_2$CO$_3$ (91 mg, 0.65 mmol) followed by 1,2,4-triazole (61 mg, 0.87 mmol) at RT under an inert atmosphere. The reaction mixture was then heated to 75° C. and stirred for 7 h. After complete consumption of the starting material (by TLC), the reaction mixture was cooled to RT, diluted with water and extracted with EtOAc (3×75 mL). The combined organic extracts were dried over anhydrous Na$_2$SO$_4$ and concentrated under reduced pressure to obtain the crude product.

The crude material was purified by silica gel column chromatography (eluent: 40% EtOAc/Hexane) to afford 17 (160 mg, 0.303 mmol, 70%) as an off-white solid.

Chiral Preparative HPLC of Enantiomers

The enantiomers of 17 (100 mg, 0.18 mmol) were separated by normal-phase preparative HPLC (Chiralpak IC, 250×19 mm, 5μ; using (A) n-hexane-(B) IPA (A:B 60:40) as a mobile phase; flow rate: 15 mL/min, λ=265 nm) to obtain desired 17(+) (28 mg) (Fraction-II) and 17(−) (28 mg) (Fraction-I).

Analytical Data for 17(+):
$^1$H NMR (500 MHz, CDCl$_3$): 8.72 (s, 1H), 8.16 (s, 1H), 7.92 (dd, J=8.5, 2.0 Hz, 1H), 7.69 (s, 1H), 7.61 (d, J=8.0 Hz, 1H), 7.55 (d, J=8.0 Hz, 2H), 7.52-7.47 (m, 1H), 7.08 (d, J=9.0 Hz, 2H), 6.77-6.70 (m, 3H), 5.38 (d, J=14.5 Hz, 1H), 4.89 (d, J=14.5 Hz, 1H), 4.42 (q, J=8.0 Hz, 2H). HPLC: 99.86%. MS (ESI): m/z 527 [M$^+$+1]. Chiral HPLC: 99.9% ee; R$_t$=13.9 min (Chiralpak IC, 250×4.6 mm, 5μ; mobile phase (A) n-Hexane-(B) IPA A:B 60:40; flow rate: 1 mL/min, WL 265 nm).
Optical rotation [α]$_D^{24.5}$: +13.96° (C=0.1% w/v in MeOH).

Example 18

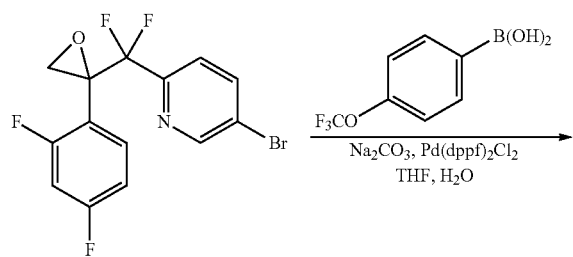

2-(2,4-Difluorophenyl)-1,1-difluoro-3-(1H-1,2,4-triazol-1-yl)-1-(5-(4-(trifluoromethoxy)phenyl)pyridin-2-yl) propan-2-ol (18)

To a stirred solution of epoxy bromide C (0.7 g, 1.93 mmol) in THF:H$_2$O (24 mL, 7:5 mixture) was added (4-(trifluoromethoxy)phenyl)boronic acid (398 mg, 1.93 mmol) followed by Pd(dppf)$_2$Cl$_2$ (394 mg, 0.48 mmol) and Na$_2$CO$_3$ (526 mg, 4.83 mmol) at RT. The mixture was degassed with argon for 45 min and then was stirred for 3 h at reflux temperature. After complete consumption of the starting material (by TLC), the reaction mixture was cooled to RT, diluted with EtOAc (20 mL) and filtered through a celite bed. The collected filtrate was washed with water and brine, dried over anhydrous Na$_2$SO$_4$ and concentrated under reduced pressure to obtain the crude product. The crude material was purified by silica gel column chromatography (eluent: 5% EtOAc/hexane) to afford compound Q (0.65 g, 1.46 mmol, 76%) as an off-white solid. $^1$H NMR (500 MHz, CDCl$_3$): δ 8.86 (s, 1H), 7.91 (dd, J=7.5, 2.0 Hz, 1H), 7.62 (d, J=8.5 Hz, 2H), 7.57 (d, J=7.5 Hz, 1H), 7.44-7.40 (m, 1H), 7.36 (d, J=8.5 Hz, 2H), 6.86-6.83 (m, 1H), 6.77-6.73 (m, 1H), 3.49 (d, J=5.0 Hz, 1H), 3.00 (d, J=5.5 Hz, 1H). MS (ESI): m/z 444 [M$^+$+1].

To a stirred solution of compound Q (0.2 g, 0.45 mmol) in DMF (5 mL) was added K$_2$CO$_3$ (62 mg, 0.45 mmol) followed by 1,2,4-triazole (46 mg, 0.67 mmol) at RT under an inert atmosphere. The reaction mixture was then heated to 70° C. and stirred for 3 h. After consumption of the starting material (by TLC), the reaction mixture was concentrated under reduced pressure, diluted with EtOAc (20 mL), and washed with water and brine. The organic layer was dried over anhydrous Na$_2$SO$_4$ and concentrated under reduced pressure to obtain the crude product. The crude material was purified by silica gel column chromatography (eluent: 30% EtOAc/hexane) to afford 18 (0.15 g, 0.29 mmol, 64.9%) as an off-white solid. $^1$H NMR (500 MHz, CDCl$_3$): δ 8.74 (s, 1H), 8.16 (s, 1H), 7.94 (dd, J=8.0, 2.0 Hz, 1H), 7.70 (s, 1H), 7.64 (d, J=8.5 Hz, 1H), 7.60 (d, J=8.0 Hz, 2H), 7.51-7.46 (m, 1H), 7.36 (d, J=8.5 Hz, 2H), 6.77-6.70 (m, 2H), 6.60 (s, 1H), 5.39 (d, J=14.5 Hz, 1H), 4.91 (d, J=14.5 Hz, 1H). MS (ESI): m/z 513 [M$^+$+1]. HPLC: 98.86%.

Example 19

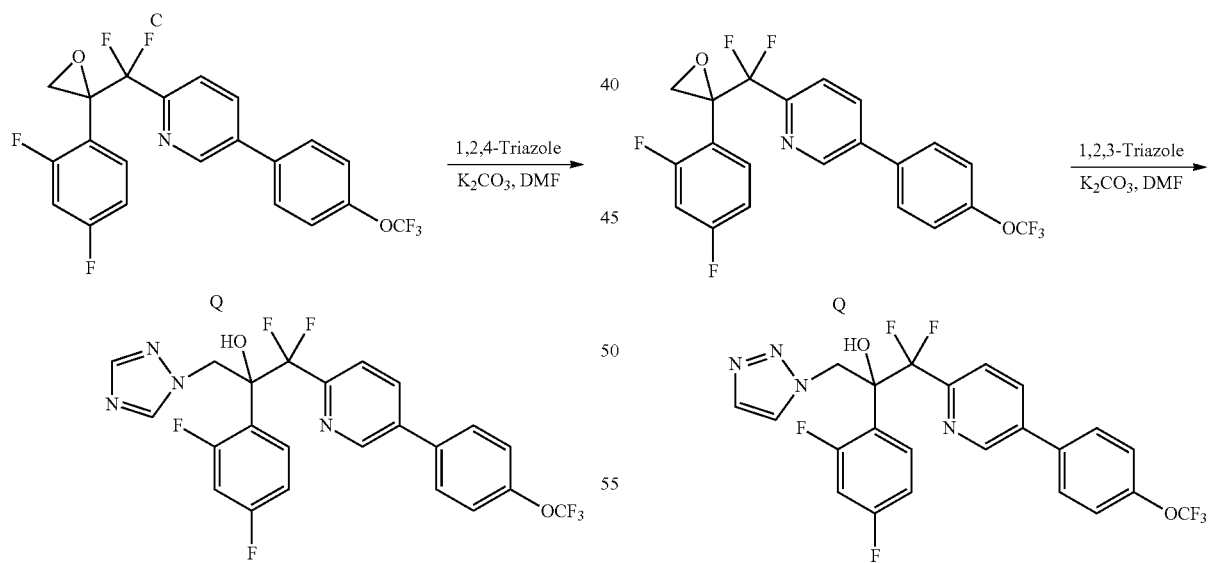

2-(2,4-Difluorophenyl)-1,1-difluoro-3-(1H-1,2,3-triazol-1-yl)-1-(5-(4-(trifluoromethoxy)phenyl) pyridin-2-yl)propan-2-ol (19)

To a stirred solution of compound Q (0.2 g, 0.45 mmol) in DMF (5 mL) was added K$_2$CO$_3$ (62 mg, 0.45 mmol) followed by 1,2,3-triazole (46 mg, 0.67 mmol) at RT under an inert atmosphere. The reaction mixture was then heated to 70° C. and stirred for 3 h. After consumption of the starting material (by TLC), the reaction mixture was concentrated under reduced pressure, diluted with EtOAc (20 mL), and washed with water and brine. The organic layer was dried over anhydrous $Na_2SO_4$ and concentrated under reduced pressure to obtain the crude product. The crude material was purified by silica gel column chromatography (eluent: 30% EtOAc/Hexane) to afford 19 (0.1 g, 0.19 mmol, 43%) as an off-white solid. $^1$H NMR (500 MHz, $CDCl_3$): δ 8.71 (s, 1H), 7.95 (d, J=8.0 Hz, 1H), 7.68 (s, 1H), 7.67 (d, J=6.0 Hz, 1H) 7.59 (d, J=8.5 Hz, 2H), 7.51 (s, 1H), 7.49-7.45 (m, 1H), 7.36 (d, J=8.5 Hz, 2H), 6.77-6.69 (m, 3H), 5.55 (d, J=14.5 Hz, 1H), 5.12 (d, J=14.5 Hz, 1H). MS (ESI): m/z 513 [M$^+$+1]. HPLC: 98.99%.

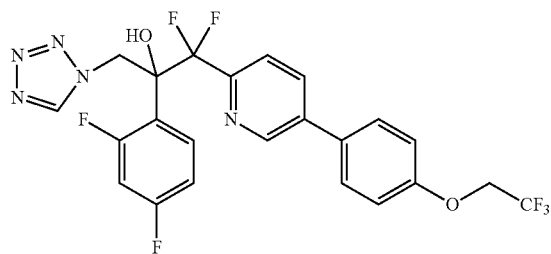 [SMILES: OC(Cn1cnnn1)(c1ccc(F)cc1F)C(F)(F)c1ccc(-c2ccc(OCC(F)(F)F)cc2)cn1]

Example 20

2-(2,4-Difluorophenyl)-1,1-difluoro-3-(2H-tetrazol-2-yl)-1-(5-(4-(2,2,2-trifluoroethoxy)phenyl)pyridin-2-yl)propan-2-ol (20)

Compound 20 was prepared using the same conditions as compound 1 from P and tetrazole (0.020 g). $^1$H NMR (500 MHz, $CDCl_3$): δ 8.74 (s, 1H), 8.31 (s, 1H), 7.95 (dd, J=8.0, 2.0 Hz, 1H), 7.66 (d, J=8.0 Hz, 1H), 7.55 (d, J=9.0 Hz, 2H), 7.48-7.43 (m, 1H), 7.08 (d, J=9.0 Hz, 2H), 7.00 (s, 1H), 6.84-6.69 (m, 2H), 5.83 (d, J=14.0 Hz, 1H), 5.41 (d, J=14.0 Hz, 1H), 4.42 (q, J=8.5 Hz, 2H). MS (ESI): m/z 528 [M$^+$+1]. HPLC: 94.47%.

Example 21

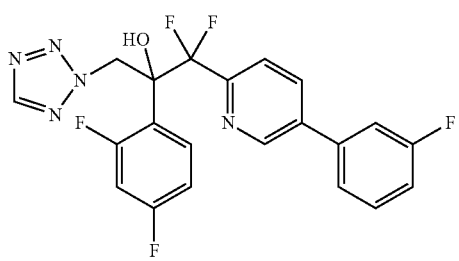 [SMILES: OC(Cn1ncnn1)(c1ccc(F)cc1F)C(F)(F)c1ccc(-c2cccc(F)c2)cn1]

2-(2,4-Difluorophenyl)-1,1-difluoro-1-(5-(3-(fluorophenyl)pyridin-2-yl)-3-(2H-tetrazol-2-yl)propan-2-ol (21)

Compound 21 was prepared using the same conditions as compound 1 (0.017 g). $^1$H NMR (500 MHz, $CDCl_3$): δ 8.76 (s, 1H), 8.32 (s, 1H), 7.98 (d, J=8.0 Hz, 1H), 7.68 (dd, J=8.5, 4.0 Hz, 1H), 7.51-7.42 (m, 2H), 7.36 (d, J=8.0 Hz, 1H), 7.29-7.28 (m, 1H), 7.18-7.15 (m, 1H), 6.84-6.79 (m, 2H), 6.73-6.69 (m, 1H), 5.84 (d, J=14.0 Hz, 1H), 5.42 (d, J=14.0 Hz, 1H). MS (ESI): m/z 448.1 [M$^+$+1]. HPLC: 98.60%.

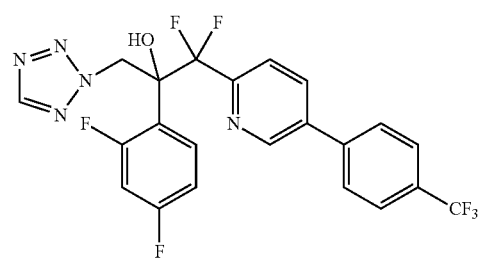 [SMILES: OC(Cn1ncnn1)(c1ccc(F)cc1F)C(F)(F)c1ccc(-c2ccc(C(F)(F)F)cc2)cn1]

Example 22

2-(2,4-Difluorophenyl)-1,1-difluoro-3-(2H-tetrazol-2-yl)-1-(5-(4-(trifluoromethylphenyl)pyridin-2-yl)propan-2-ol (22)

Compound 22 was prepared using the same conditions as compound 1 (0.020 g). $^1$H NMR (500 MHz, $CDCl_3$): δ 8.78 (s, 1H), 8.32 (s, 1H), 8.02 (dd, J=8.0, 2.0 Hz, 1H), 7.78 (d, J=8.5 Hz, 2H), 7.72-7.68 (m, 3H), 7.48-7.43 (m, 1H), 6.84-6.79 (m, 1H), 6.73-6.71 (m, 1H), 6.69 (s, 1H), 5.85 (d, J=14.0 Hz, 1H), 5.42 (d, J=14.0 Hz, 1H). MS (ESI): m/z 498.0 [M$^+$+1]. HPLC: 97.72%.

Example 23

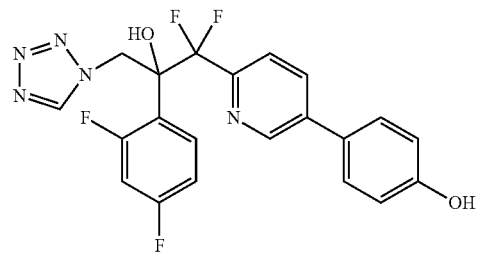 [SMILES: Oc1ccc(-c2ccc(C(F)(F)C(O)(Cn3cnnn3)c3ccc(F)cc3F)nc2)cc1]

4-(6-(2-(2,4-Difluorophenyl)-1,1-difluoro-2-hydroxy-3-(1H-tetrazol-1-yl)propyl)pyridin-3-yl)phenol (23)

Compound 23 was prepared using the same conditions as compound 1 (0.0109 g). $^1$H NMR (500 MHz, $CDCl_3$): δ 8.76 (s, 1H), 8.69 (s, 1H), 7.94 (dd, J=8.5, 2.5 Hz, 1H), 7.80 (s, 1H), 7.62 (d, J=8.0 Hz, 1H), 7.45 (d, J=8.5 Hz, 2H), 7.41-7.36 (m, 1H), 6.96 (d, J=8.5 Hz, 2H), 6.79-6.75 (m, 1H), 6.69-6.65 (m, 1H), 5.60 (d, J=14.0 Hz, 1H), 5.17 (br s, 1H), 5.13 (d, J=14.0 Hz, 1H). MS (ESI): m/z 445.9 [M$^+$+1]. HPLC: 98.55%.

Example 24

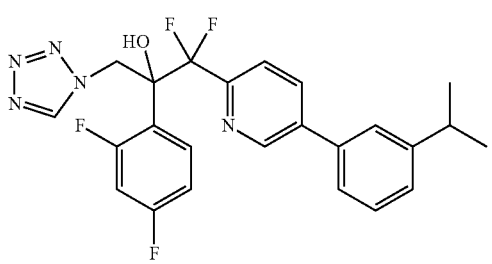 [SMILES: CC(C)c1cccc(-c2ccc(C(F)(F)C(O)(Cn3cnnn3)c3ccc(F)cc3F)nc2)c1]

2-(2,4-Difluorophenyl)-1,1-difluoro-1-(5-(3-isopropylphenyl)pyridin-2-yl)-3-(1H-tetrazol-1-yl)propan-2-ol (24)

Compound 24 was prepared using the same conditions as compound 1 (0.020 g). $^1$H NMR (500 MHz, CDCl$_3$): δ 8.76 (s, 1H), 8.75 (s, 1H), 7.99 (d, J=8.0 Hz, 1H), 7.79 (s, 1H), 7.65 (d, J=8.0 Hz, 1H), 7.45-7.33 (m, 5H), 6.79-6.75 (m, 1H), 6.68-6.65 (m, 1H), 5.62 (d, J=14.5 Hz, 1H), 5.12 (d, J=14.5 Hz, 1H), 3.02-2.96 (m, 1H), 1.30 (d, J=7.0 Hz, 6H). MS (ESI): m/z 472.1 [M$^+$+1]. HPLC: 99.50%.

Example 25

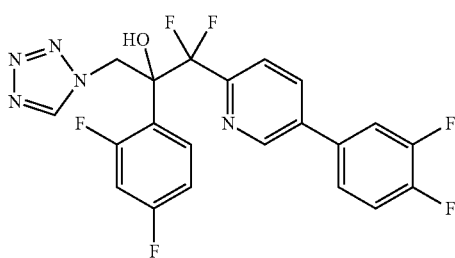 [SMILES: OC(Cn1cnnn1)(c1ccc(F)cc1F)C(F)(F)c1ccc(-c2ccc(F)c(F)c2)cn1]

2-(2,4-Difluorophenyl)-1-(5-(3,4-difluorophenyl)pyridin-2-yl)-1,1-difluoro-3-(1H-tetrazol-1-yl)propan-2-ol (25)

Compound 25 was prepared using the same conditions as compound 1 (0.029 g). $^1$H NMR (500 MHz, CDCl$_3$): δ 8.75 (s, 1H), 8.67 (s, 1H), 7.94 (dd, J=8.0, 2.0 Hz, 1H), 7.67 (d, J=8.0 Hz, 1H), 7.58 (br s, 1H), 7.42-7.36 (m, 2H), 7.34-7.29 (m, 2H), 6.80-6.76 (m, 1H), 6.71-6.67 (m, 1H), 5.56 (d, J=14.5 Hz, 1H), 5.17 (d, J=14.5 Hz, 1H). MS (ESI): m/z 466.0 [M$^+$+1]. HPLC: 98.94%.

Example 26

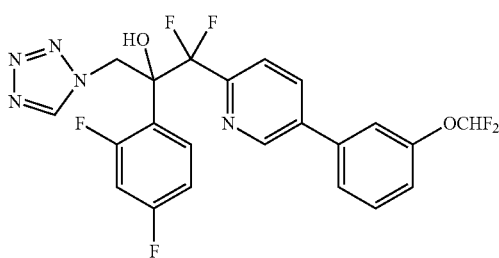 [SMILES: OC(Cn1cnnn1)(c1ccc(F)cc1F)C(F)(F)c1ccc(-c2cccc(OC(F)F)c2)cn1]

1-(5-(3-(Difluoromethoxy)phenyl)pyridin-2-yl)-2-(2,4-difluorophenyl)-1,1-difluoro-3-(1H-tetrazol-1-yl)propan-2-ol (26)

Compound 26 was prepared using the same conditions as compound 1 (0.022 g). $^1$H NMR (500 MHz, CDCl$_3$): δ 8.79 (s, 1H), 8.77 (s, 1H), 7.98 (d, J=8.0 Hz, 1H), 7.67 (d, J=8.0 Hz, 1H), 7.57 (s, 1H), 7.51 (dd, J=8.0, 2.0 Hz, 1H), 7.41-7.35 (m, 2H), 7.31 (s, 1H), 7.25-7.22 (m, 1H), 6.79-6.74 (m, 1H), 6.69-6.62 (m, 1H), 6.59 (t, J=74.0 Hz, 1H), 5.58 (d, J=14.0 Hz, 1H), 5.17 (d, J=14.0 Hz, 1H). MS (ESI): m/z 496.0 [M$^+$+1]. HPLC: 92.30%.

Example 27

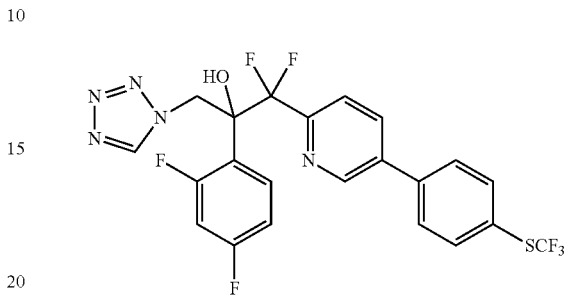

2-(2,4-Difluorophenyl)-1,1-difluoro-3-(1H-tetrazol-1-yl)-1-(5-(4-((trifluoromethyl)thio)phenyl)pyridin-2-yl)propan-2-ol (27)

Compound 27 was prepared using the same conditions as compound 1 (0.031 g). $^1$H NMR (500 MHz, CDCl$_3$): δ 8.76 (s, 1H), 8.73 (s, 1H), 8.01 (d, J=8.0 Hz, 1H), 7.80 (d, J=8.5 Hz, 2H), 7.70 (d, J=8.0 Hz, 1H), 7.61 (d, J=8.5 Hz, 2H), 7.50 (br s, 1H), 7.42-7.37 (m, 1H), 6.80-6.76 (m, 1H), 6.70-6.67 (m, 1H), 5.56 (d, J=14.5 Hz, 1H), 5.18 (d, J=14.5 Hz, 1H). MS (ESI): m/z 530.0 [M$^+$+1]. HPLC: 96.42%.

Compounds 28-36 in Table 1 were prepared using the same conditions as compound 1 from intermediate C and commercially available boronic acids and azoles.

Compounds 37-42 in Table 1 were prepared using the same conditions as compound 12 from intermediate E and commercially available aryl bromides and azoles.

Compounds 43-45 in Table 1 were prepared using the same conditions as compound 12 from intermediate E and aryl bromides that have been synthesized via alkylation like intermediate F and commercially available azoles.

Example 46

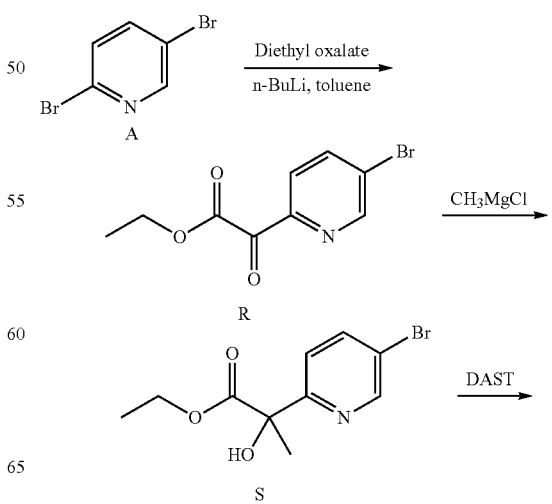

-continued

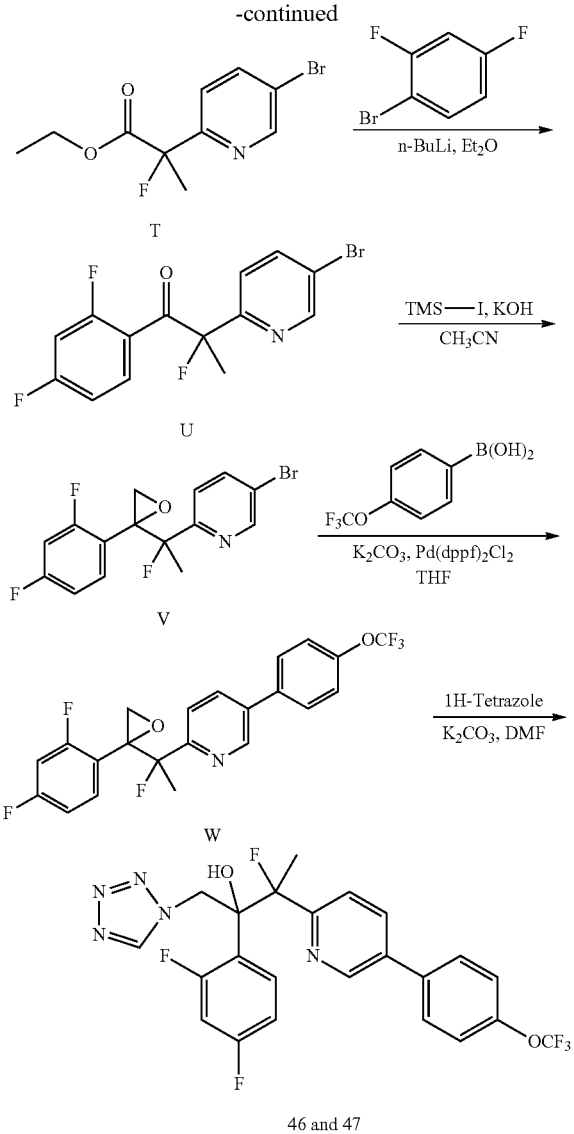

2-(2,4-Difluorophenyl)-3-fluoro-1-(1H-tetrazol-1-yl)-3-(5-(4-(trifluoromethoxy)phenyl)-pyridin-2-yl)butan-2-ol (46 and 47)

To a stirred solution of 2,5-dibromopyridine (A; 30 g, 126.5 mmol) in toluene (1.5 L) was added n-BuLi (79 mL, 126 mmol; 1.6 M solution) dropwise at −78° C. under an inert atmosphere. After being stirred for 40 min at −78° C., diethyl oxalate (20.6 mL, 126.5 mmol) was added to the reaction mixture at −78° C. and stirring was continued for another 20 min. After completion of the reaction (by TLC), the reaction mixture was quenched with saturated NH$_4$Cl solution and extracted with EtOAc (2×1.0 L). The combined organic extracts were washed with water and brine, dried over anhydrous Na$_2$SO$_4$ and concentrated under reduced pressure to obtain the crude product. The crude material was purified by silica gel column chromatography (eluent: 15-55% EtOAc/hexanes) to afford R (13 g, 50.37 mmol, 38%). $^1$H NMR (200 MHz, CDCl$_3$): δ 8.81 (d, J=1.4 Hz, 1H), 8.17-7.98 (m, 2H), 4.48 (q, J=7.4 Hz, 2H), 1.41 (t, J=7.4 Hz, 3H). MS (ESI): m/z 259 [M+1]$^+$.

To a stirred solution of R (13 g, 50.3 mmol) in THF (150 mL) was added methyl magnesium chloride (CH$_3$MgCl; 15 mL, 50.3 mmol; 3 M solution in THF) at −5° C. under an inert atmosphere. Stirring was continued for another 2 h. Progress of the reaction was monitored by TLC. The reaction mixture was then quenched with saturated NH$_4$Cl solution and extracted with EtOAc (2×200 mL). The combined organic extracts were washed with water and brine, dried over anhydrous Na$_2$SO$_4$ and concentrated under reduced pressure to obtain the crude product. The crude material was purified by silica gel column chromatography (eluent: 15-55% EtOAc/hexanes) to afford S (2.8 g, 10.76 mmol, 21%). $^1$H NMR (200 MHz, CDCl$_3$): δ 8.61 (d, J=1.4 Hz, 1H), 7.84 (dd, J=8.0, 1.4 Hz, 1H), 7.49 (d, J=8.0 Hz, 1H), 4.92 (br s, 1H), 4.20 (q, J=7.4 Hz, 2H), 1.80 (s, 3H), 1.22 (t, J=7.4 Hz, 3H).

To a stirred solution of S (2.8 g, 10.7 mmol) in CH$_2$Cl$_2$ (50 mL) was added diethylaminosulfur trifluoride (DAST; 3.5 mL, 26.5 mmol) at 0° C. under an inert atmosphere, and the reaction mixture was stirred for 16 h at RT. Progress of the reaction was monitored by TLC. The reaction mixture was then quenched with ice-cold water and extracted with CH$_2$Cl$_2$ (2×100 mL). The combined organic extracts were washed with water and brine, dried over anhydrous Na$_2$SO$_4$ and concentrated under reduced pressure. The crude material was purified by silica gel column chromatography (eluent: 15-55% EtOAc/hexanes) to afford T (2.1 g, 7.6 mmol, 75%). $^1$H NMR (200 MHz, CDCl$_3$): δ 8.62 (d, J=1.4 Hz, 1H), 7.85 (dd, J=8.0, 1.4 Hz, 1H), 7.50 (d, J=8.0 Hz, 1H), 4.23 (q, J=7.4 Hz, 2H), 1.95 (d, J$_{F,H}$=24.0 Hz, 3H), 1.24 (t, J=7.4 Hz, 3H). MS (ESI): m/z 276 [M]$^+$ To a stirred solution of 1-bromo-2,4-difluorobenzene (0.9 mL, 8.01 mmol) in diethyl ether (50 mL) was added dropwise n-BuLi (5 mL, 8.01 mmol; 1.6 M solution) at −78° C. under an inert atmosphere. After being stirred for 40 min at −78° C., a solution of T (2.1 g, 8.01 mmol) in diethyl ether (50 mL) was added dropwise to the reaction mixture at −78° C. Stirring was continued for another 20 min. After completion of the reaction (by TLC), the reaction mixture was quenched with saturated NH$_4$Cl solution and extracted with EtOAc. The combined organic extracts were washed with water and brine, dried over anhydrous Na$_2$SO$_4$ and concentrated under reduced pressure to obtain the crude product. The crude material was purified by silica gel column chromatography (eluent: 15-55% EtOAc/hexanes) to afford ketone U (2.15 g, 6.24 mmol, 77.9%). $^1$H NMR (200 MHz, CDCl$_3$): δ 8.61 (d, J=1.6 Hz, 1H), 7.96 (dd, J=8.0, 1.6 Hz, 1H), 7.67-7.62 (m, 1H), 7.48 (d, J=8.0 Hz, 1H), 6.98-6.67 (m, 2H), 1.98 (d, J$_{F,H}$=24.0 Hz, 3H). MS (ESI): m/z 343.9 [M+1]$^+$.

To a stirred solution of ketone U (2.1 g, 6.10 mmol) in acetonitrile (CH$_3$CN; 30 mL) were added iodotrimethylsilane (TMS-I; 1.47 g, 6.71 mmol) and potassium hydroxide (KOH; 683 mg, 12.20 mmol) at RT under an inert atmosphere. The resulting reaction mixture was heated to 70° C. and stirred for 1.5 h; progress of the reaction was monitored by TLC. The reaction mixture was then diluted with EtOAc, stirred for 5 min and filtered; the filtrate was concentrated under reduced pressure to obtain the crude product. The crude material was purified by silica gel column chromatography (eluent: 15-55% EtOAc/hexanes) to afford epoxide V (1.92 g, 5.36 mmol, 88%) as a mixture of diastereomers. The product was confirmed by $^1$H-NMR spectral analysis and was taken forward to the next step without any further purification.

To a stirred solution of epoxide V (1.0 g, 2.79 mmol) in THF (15 mL) and water (5 mL) were added (4-(trifluoromethoxy) phenyl)boronic acid (575 mg, 2.79 mmol), K$_2$CO$_3$ (770 mg, 5.58 mmol) and Pd(dppf)$_2$Cl$_2$ (102 mg, 0.139 mmol) at RT under an inert atmosphere. The reaction mixture was degassed for 30 min by purging with argon. The reaction mixture was then heated to 65° C. and stirred for 2 h; progress of the reaction was monitored by TLC. The reaction mixture was then cooled to RT, diluted with water and extracted with EtOAc (2×30 mL). The combined organic layer was washed with water and brine, dried over anhydrous $Na_2SO_4$ and concentrated under reduced pressure to obtain the crude product. The crude compound was purified by silica gel column chromatography to afford W (0.9 g, 2.05 mmol, 79%) as a mixture of diastereomers. The product was confirmed by $^1$H-NMR and MS analyses and was taken forward to the next step without any further purification. MS (ESI): m/z 440 [M+1]$^+$.

To a stirred solution of W (900 mg, 2.05 mmol) in DMF (10 mL) was added 1H-tetrazole (215 mg, 3.07 mmol) followed by $K_2CO_3$ (283 mg, 2.05 mmol) at RT under an inert atmosphere. The resulting reaction mixture was heated to 65° C. and stirred for 48 h; progress of the reaction was monitored by TLC. The reaction mixture was then cooled to RT, diluted with water and extracted with EtOAc (2×50 mL). The combined organic layers were washed with water and brine, dried over anhydrous $Na_2SO_4$ and concentrated under reduced pressure to obtain the crude product. The crude material was purified by silica gel column chromatography to afford the desired diastereomers 46 (110 mg, 0.21 mmol, 11%) and 47 (120 mg, 0.23 mmol, 11.5%). 46: $^1$H NMR (500 MHz, CDCl$_3$): δ 8.68 (s, 1H), 8.60 (s, 1H), 8.07 (d, J=8.5 Hz, 1H), 7.85-7.78 (m, 3H), 7.63 (d, J=8.5 Hz, 2H), 7.38 (d, J=8.5 Hz, 2H), 6.90-6.87 (m, 1H), 6.85-6.81 (m, 1H), 5.47 (d, J=14.5 Hz, 1H), 4.41 (d, J=14.5 Hz, 1H), 1.50 (d, J$_{F-H}$=23.5 Hz, 3H). MS (ESI): m/z 510 [M+1]$^+$. HPLC: 99.73%. 47: $^1$H NMR (500 MHz, CDCl$_3$): δ 8.73 (s, 1H), 8.66 (s, 1H), 7.76 (dd, J=8.5, 2.0 Hz, 1H), 7.53 (d, J=8.5 Hz, 2H), 7.40 (br s, 1H), 7.33-7.25 (m, 3H), 6.89-6.85 (m, 1H), 6.64-6.60 (m, 1H), 6.41-6.38 (m, 1H), 5.76 (d, J=14.5 Hz, 1H), 5.00 (d, J=14.5 Hz, 1H), 1.98 (d, J$_{F-H}$=22.5 Hz, 3H). MS (ESI): m/z 510 [M+H]$^+$. HPLC: 99.48%.

Compounds 48-57 in Table 1 were prepared using the same conditions as compound 46 from intermediate V and commercially available boronic acids and azoles.

Example 58

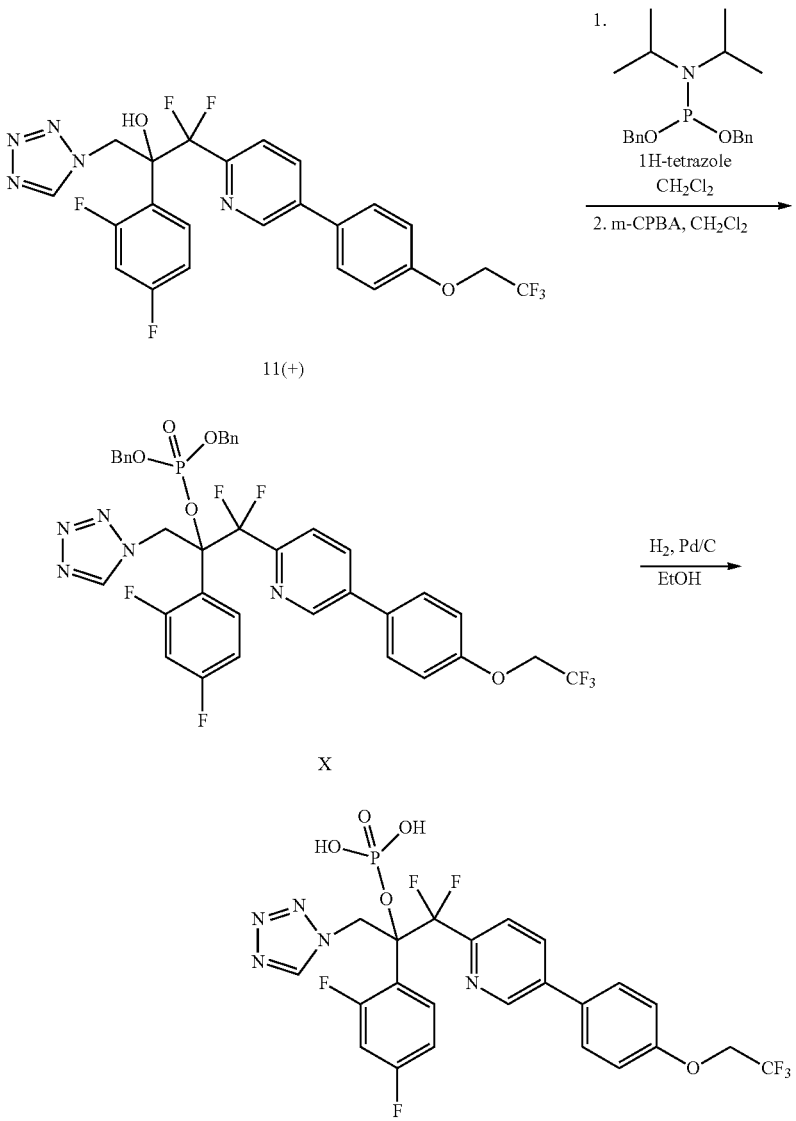

2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl dihydrogen phosphate (58)

To a suspension of 11(+) (200 mg, 0.38 mmol) and 1H-tetrazole (106 mg, 1.51 mmol) in anhydrous CH$_2$Cl$_2$ (15 mL) was added a solution of dibenzyl-N,N-diisopropylphosphoramidite (0.38 mL, 1.14 mmol) in CH$_2$Cl$_2$ (5 mL). After 48 h, the reaction mixture was cooled to −5° C., and a solution of 3-chloroperoxybenzoic acid (m-CPBA; 195 mg, 1.14 mmol) in CH$_2$Cl$_2$ (5 mL) was added slowly. After 1 h, the mixture was diluted with CH$_2$Cl$_2$ (30 mL), washed with 5% aqueous Na$_2$S$_2$O$_5$ (2×30 mL), 10% aqueous NaHCO$_3$ (2×30 mL) and brine (30 mL) and then dried over anhydrous Na$_2$SO$_4$. The organic solvent was evaporated in vacuo, and the obtained crude material was purified by preparative HPLC to afford compound X (125 mg, 0.16 mmol, 42%) as colorless semisolid. $^1$H NMR (500 MHz, CDCl$_3$): δ 9.12 (s, 1H), 8.82 (s, 1H), 7.75 (d, J=8.5 Hz, 1H), 7.55 (d, J=9.0 Hz, 2H), 7.37 (m, 5H), 7.31-7.18 (m, 7H), 7.08 (d, J=9.0 Hz, 2H), 6.70-6.58 (m, 2H), 6.24 (d, J=16.0 Hz, 1H), 5.97 (d, J=16.0 Hz, 1H), 5.25-5.18 (m, 2H), 4.97-4.84 (m, 2H), 4.42 (q, J=8.5 Hz, 2H). $^{31}$P NMR (500 MHz, CDCl$_3$): δ −14.29 (s); HPLC: 99%. MS (ESI): m/z 788 [M+H]$^+$.

A mixture of compound X (250 mg, 0.32 mmol) and 10% Pd/C (50 mg) in EtOH (10 mL) was stirred under hydrogen (1 atm) for 3 h. The catalyst was removed by filtration over a pad of Celite®, and the filter cake was washed with EtOH (5 mL) and EtOAc (5 mL). The combined filtrates were evaporated in vacuo, and the residue was triturated with n-pentane to give 58 (140 mg, 0.23 mmol, 72%) as a white solid. $^1$H NMR (500 MHz, DMSO-d$_6$): δ 9.39 (s, 1H), 8.90 (s, 1H), 8.19 (d, J=8.0 Hz, 1H), 7.79 (d, J=9.0 Hz, 2H), 7.52 (d, J=8.0 Hz, 1H), 7.35-7.30 (m, 1H), 7.21-7.14 (m, 3H), 6.98-6.95 (m, 1H), 6.18 (d, J=15.5 Hz, 1H), 5.79 (d, J=15.5 Hz, 1H), 4.85 (q, J=9.0 Hz, 2H). $^{31}$P NMR (500 MHz, DMSO-d$_6$): δ −6.57 (s). HPLC: 99%. MS (ESI): m/z 608 [M+H]$^+$.

HPLC Method A Specifications
Column: Aquity BEH C-18 (50×2.1 mm, 1.70
Mobile Phase: A) Acetonitrile; B) 0.025% aqueous (aq) trifluoroacetic acid (TFA)
Flow Rate: 0.50 mL/min
Time (min) % B: 0.01/90, 0.5/90, 3/10, 6/10
HPLC Method O Specifications:
Column: Zorbax Phenyl Hexyl (50×4.6 mm, 1.8µ)
Mobile Phase: A) Acetonitrile; B) 0.1% as TFA
Flow Rate: 1.00 mL/min
Time (min) % B: 0.01/50, 1/50, 4/10, 10/10

TABLE 1

Structures for Example Compounds

| Example Number | Structure |
|---|---|
| 28 | 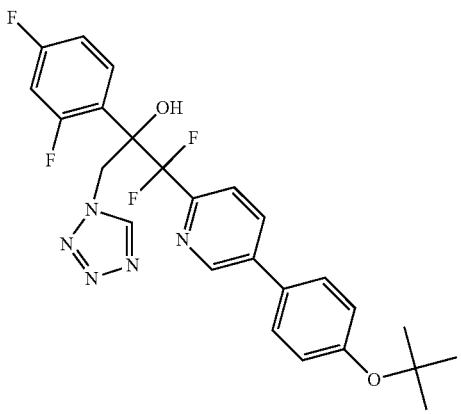 [SMILES: CC(C)(C)Oc1ccc(-c2ccc(C(F)(F)C(O)(Cn3cnnn3)c3ccc(F)cc3F)nc2)cc1] |
| 29 | 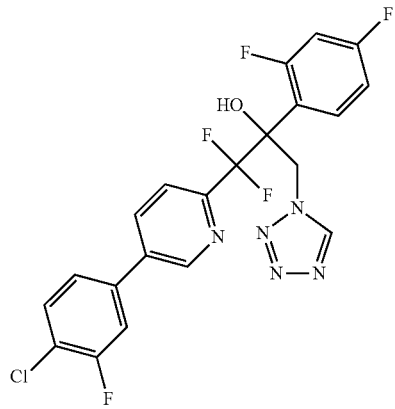 [SMILES: OC(Cn1cnnn1)(c1ccc(F)cc1F)C(F)(F)c1ccc(-c2ccc(Cl)c(F)c2)cn1] |

TABLE 1-continued
Structures for Example Compounds
| Example Number | Structure |
|---|---|
| 30 | 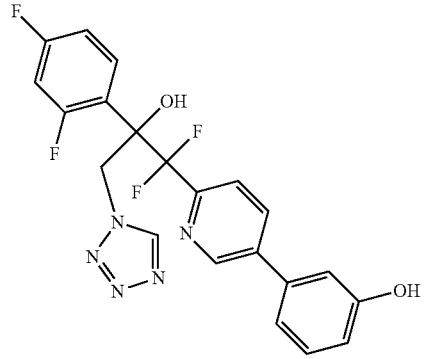 [SMILES: Oc1cccc(-c2ccc(C(F)(F)C(O)(Cn3cnnn3)c3ccc(F)cc3F)nc2)c1] |
| 31 | 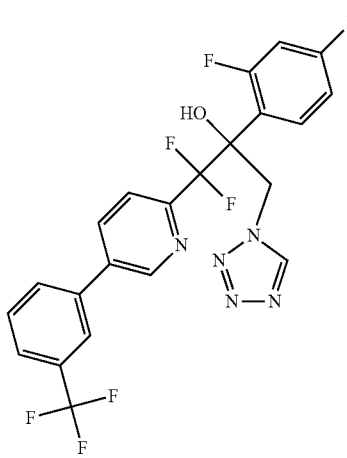 |
| 32 | 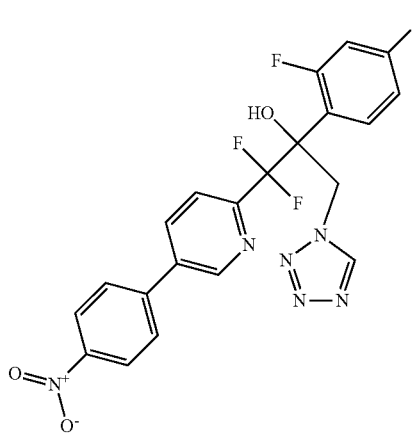 |

TABLE 1-continued
Structures for Example Compounds
| Example Number | Structure |
| --- | --- |
| 33 | 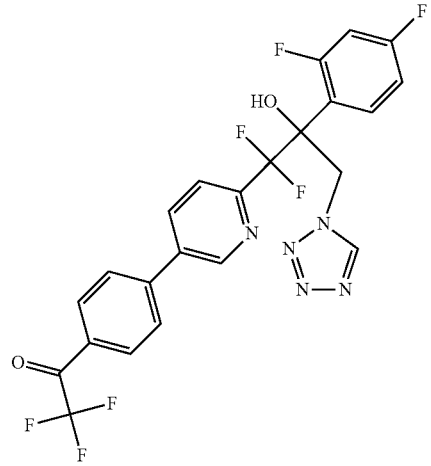 [SMILES: O=C(c1ccc(-c2ccc(C(F)(F)C(O)(Cn3cnnn3)c3ccc(F)cc3F)nc2)cc1)C(F)(F)F] |
| 34 | 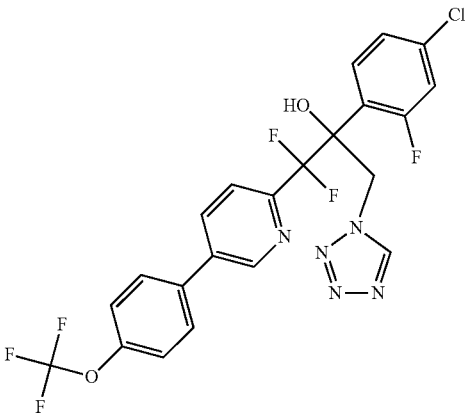 [SMILES: OC(Cn1cnnn1)(c1ccc(Cl)cc1F)C(F)(F)c1ccc(-c2ccc(OC(F)(F)F)cc2)cn1] |
| 35 | 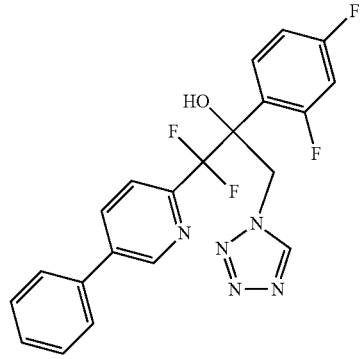 [SMILES: OC(Cn1cnnn1)(c1ccc(F)cc1F)C(F)(F)c1ccc(-c2ccccc2)cn1] |

TABLE 1-continued

Structures for Example Compounds

| Example Number | Structure |
|---|---|
| 36 | *(chemical structure)* |
| 37 | *(chemical structure)* |
| 38 | *(chemical structure)* |

TABLE 1-continued
Structures for Example Compounds
| Example Number | Structure |
|---|---|
| 39 | 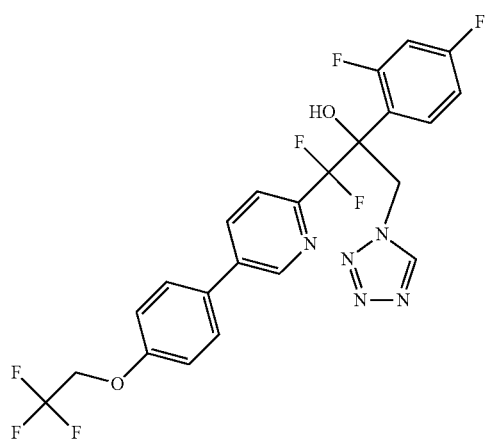 [SMILES: OC(Cn1cnnn1)(c1ccc(F)cc1F)C(F)(F)c1ccc(-c2ccc(OCC(F)(F)F)cc2)cn1] |
| 40 | 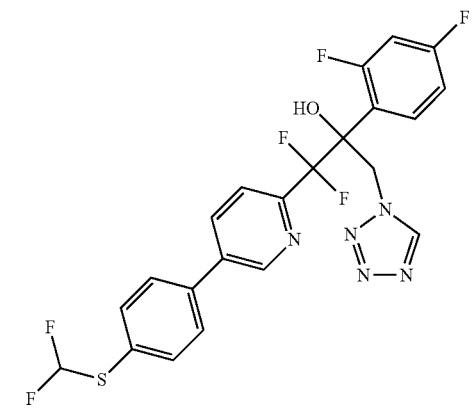 [SMILES: OC(Cn1cnnn1)(c1ccc(F)cc1F)C(F)(F)c1ccc(-c2ccc(SC(F)F)cc2)cn1] |
| 41 | 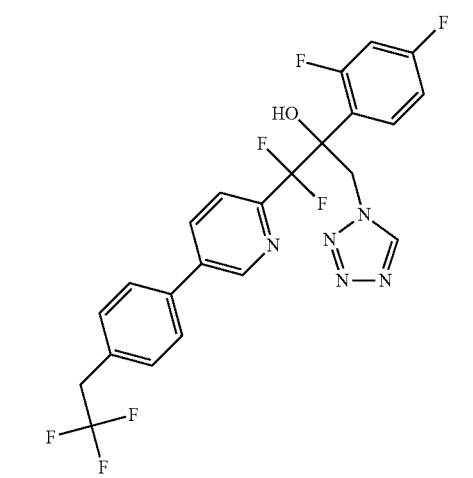 [SMILES: OC(Cn1cnnn1)(c1ccc(F)cc1F)C(F)(F)c1ccc(-c2ccc(CC(F)(F)F)cc2)cn1] |

TABLE 1-continued
Structures for Example Compounds
| Example Number | Structure |
|---|---|
| 42 | 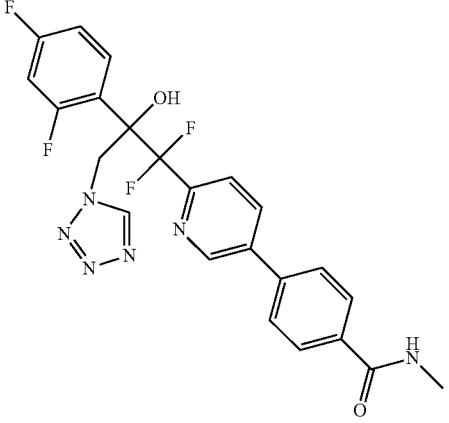 [SMILES: CNC(=O)c1ccc(-c2ccc(C(F)(F)C(O)(Cn3cnnn3)c3ccc(F)cc3F)nc2)cc1] |
| 43 | 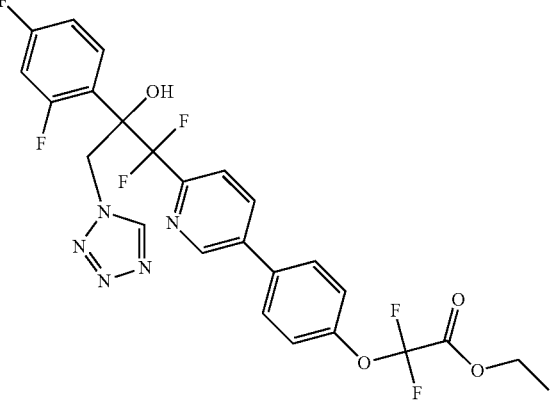 |
| 44 | 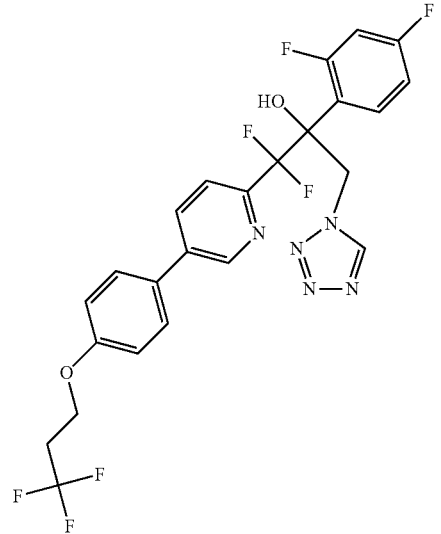 [SMILES: OC(Cn1cnnn1)(c1ccc(F)cc1F)C(F)(F)c1ccc(-c2ccc(OCCC(F)(F)F)cc2)cn1] |

TABLE 1-continued
Structures for Example Compounds
| Example Number | Structure |
|---|---|
| 45 | 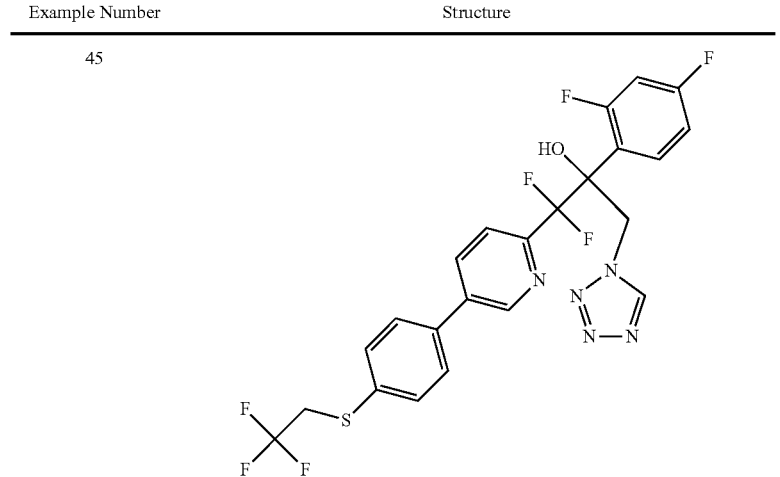 |
| 46 | 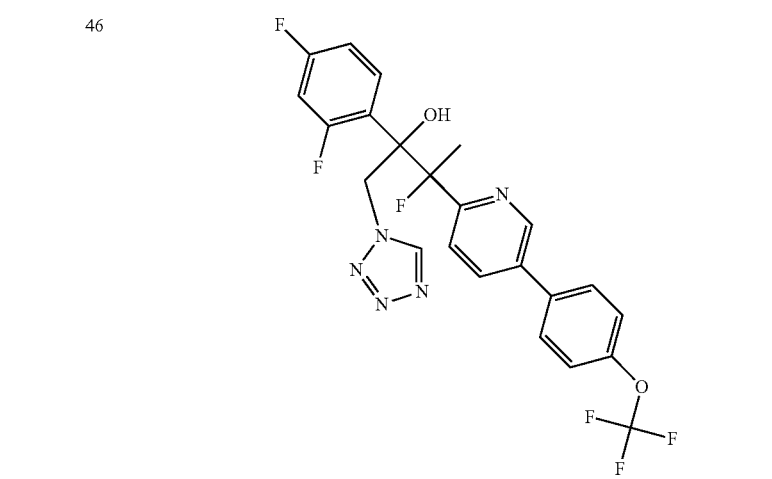 |
| 47 | 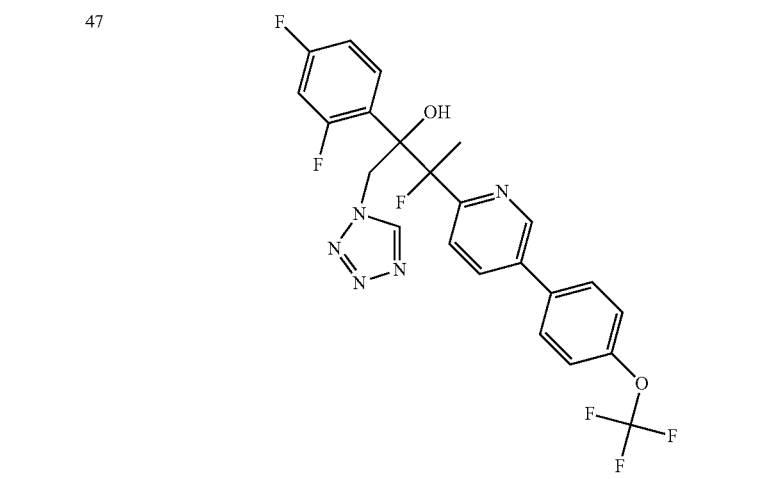 |

TABLE 1-continued

Structures for Example Compounds

| Example Number | Structure |
|---|---|
| 48 | 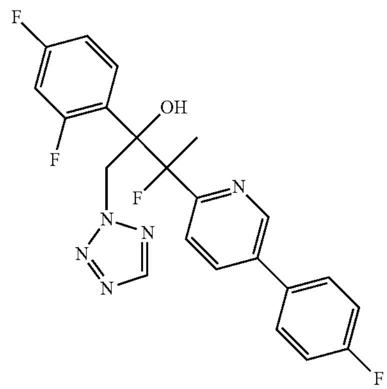 [SMILES: CC(F)(c1ccc(-c2ccc(F)cc2)cn1)C(O)(Cn1ncnn1)c1ccc(F)cc1F] |
| 49 | 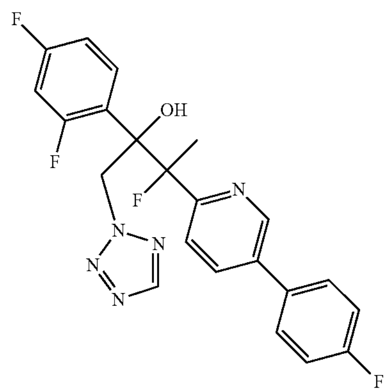 [SMILES: CC(F)(c1ccc(-c2ccc(F)cc2)cn1)C(O)(Cn1ncnn1)c1ccc(F)cc1F] |
| 50 | 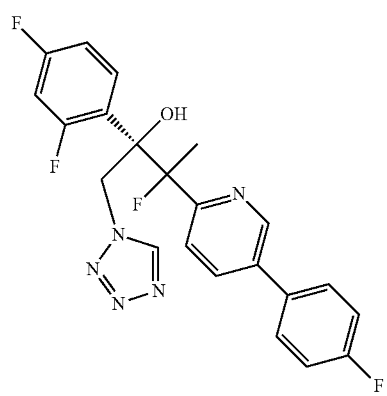 [SMILES: CC(F)(c1ccc(-c2ccc(F)cc2)cn1)[C@](O)(Cn1cnnn1)c1ccc(F)cc1F] |
| 51 | 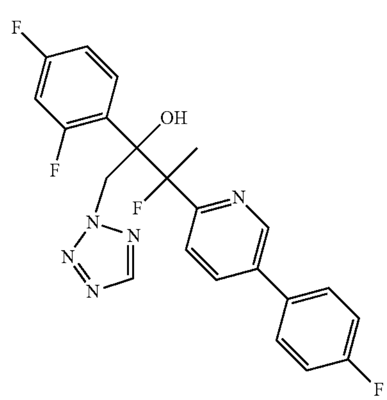 [SMILES: CC(F)(c1ccc(-c2ccc(F)cc2)cn1)C(O)(Cn1ncnn1)c1ccc(F)cc1F] |

TABLE 1-continued

Structures for Example Compounds

| Example Number | Structure |
| --- | --- |
| 52 | 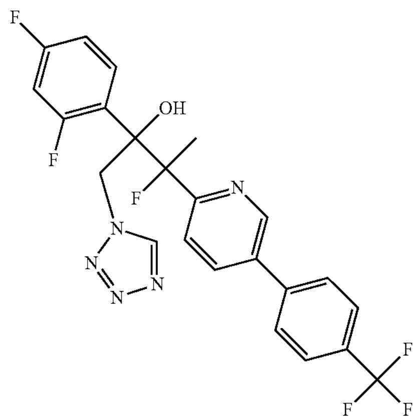 [SMILES: CC(F)(c1ccc(-c2ccc(C(F)(F)F)cc2)cn1)C(O)(Cn1cnnn1)c1ccc(F)cc1F] |
| 53 | 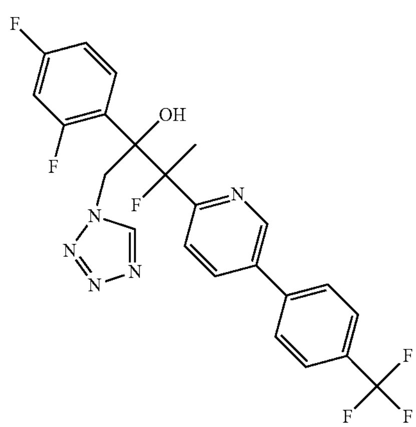 [SMILES: CC(F)(c1ccc(-c2ccc(C(F)(F)F)cc2)cn1)C(O)(Cn1cnnn1)c1ccc(F)cc1F] |
| 54 | 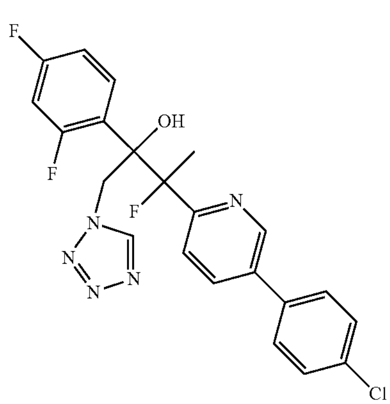 [SMILES: CC(F)(c1ccc(-c2ccc(Cl)cc2)cn1)C(O)(Cn1cnnn1)c1ccc(F)cc1F] |

TABLE 1-continued

Structures for Example Compounds

| Example Number | Structure |
| --- | --- |
| 55 | 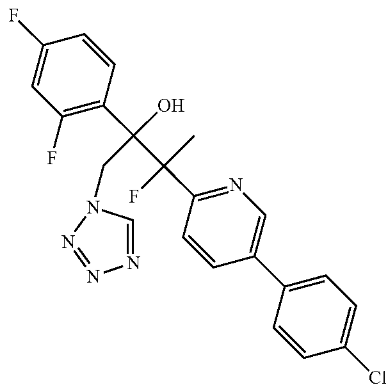 [SMILES: CC(F)(c1ccc(-c2ccc(Cl)cc2)cn1)C(O)(Cn1cnnn1)c1ccc(F)cc1F] |
| 56 | 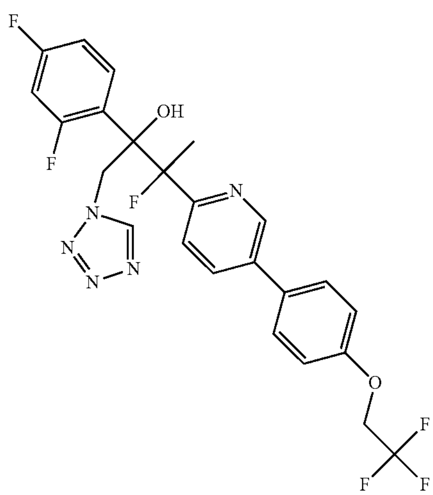 [SMILES: CC(F)(c1ccc(-c2ccc(OCC(F)(F)F)cc2)cn1)C(O)(Cn1cnnn1)c1ccc(F)cc1F] |
| 57 | 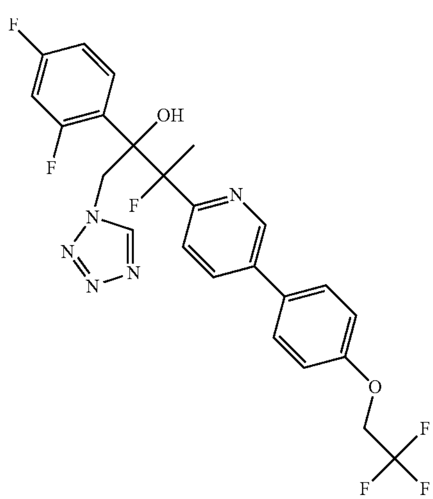 [SMILES: CC(F)(c1ccc(-c2ccc(OCC(F)(F)F)cc2)cn1)C(O)(Cn1cnnn1)c1ccc(F)cc1F] |

TABLE 1-continued

Structures for Example Compounds

| Example Number | Structure |
|---|---|
| 58 | 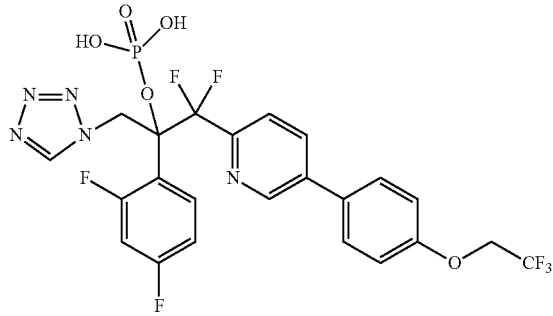 [SMILES: O=P(O)(O)OC(Cn1cnnn1)(c1ccc(F)cc1F)C(F)(F)c1ccc(-c2ccc(OCC(F)(F)F)cc2)cn1] |

TABLE 2

Analytical Data for Example Compounds in Table 1

| Example Number | HPLC Method | HPLC Retention Time (min) | ESIMS (M + H) |
|---|---|---|---|
| 28 | A | 2.9 | 501.9 |
| 29 | A | 2.77 | 482.0 |
| 30 | A | 2.26 | 446.1 |
| 31 | A | 2.76 | 498.0 |
| 32 | A | 2.51 | 475.1 |
| 33 | A | 2.3 | 526.1 |
| 34 | A | 2.95 | 531.0 |
| 35 | A | 2.54 | 430.0 |
| 36 | A | 2.46 | 515.0 |
| 37 | A | 2.52 | 541.0 |
| 38 | A | 2.64 | 496.0 |
| 39 | A | 2.82 | 513.0 |
| 40 | A | 2.74 | 512.1 |
| 41 | A | 2.75 | 512.0 |
| 42 | A | 2.05 | 487.1 |
| 43 | O | 3.81 | |
| 44 | A | 2.8 | 542.0 |
| 45 | A | 2.8 | 544.1 |
| 46 | A | 3.14 | 510.2 |
| 47 | A | 3.01 | 510.2 |
| 48 | A | 3.02 | 444.5 |
| 49 | A | 2.81 | 444.6 |
| 50 | A | 2.9 | 444.5 |
| 51 | A | 2.73 | 444.5 |
| 52 | A | 3.07 | 494.0 |
| 53 | A | 2.88 | 494.2 |
| 54 | A | 3.06 | 460.2 |
| 55 | A | 2.92 | 460.1 |
| 56 | A | 3.04 | 524.3 |
| 57 | A | 2.85 | 524.1 |
| 58 | A | 2.35 | 608 |

BIOLOGICAL ACTIVITY

A. Minimum Inhibitory Concentration (MIC) (*C. albicans*)

Compounds of the present disclosure were assessed for their ability to inhibit the growth of common strains of fungus, *C. albicans* using a standardized procedure (CLSI M27-A2). Stock solutions of the test compounds and standards were prepared in DMSO at 1,600 µg/mL (*C. albicans*). Eleven, serial, one-half dilutions of compounds were prepared in 96-well plates in RPMI+MOPS. The assay concentration ranges were 8-0.001 µg/mL (*C. albicans*). Cell suspensions of *C. albicans* were prepared and added to each well at concentrations of approximately $3.7 \times 10^3$ colony-forming- units per milliliter (cfu/mL). All testing was in duplicate. The inoculated plates were incubated for approximately 48 h at 35±1° C. At the completion of incubation the wells of each plate were evaluated visually for the presence of fungal growth.

For fluconazole and the test compounds, the MIC was the concentration at which growth was significantly reduced (about 50% reduction). For voriconazole the MIC was the concentration which reduced *C. albicans* growth by 50% (per CLSI, M27-A2). For QC purposes *C. krusei* isolate ATCC 6258 ($4.0 \times 10^3$ cfu/mL) was included in the VOR assay. This isolate did not exhibit trailing growth against voriconazole, therefore the MIC was the concentration at which growth was completely inhibited.

B. Minimum Inhibitory Concentration (MIC) (*Septoria tritici*)

Compounds of the present disclosure were assessed for their ability to inhibit the growth of a common strain of the fungal plant pathogen *Septoria tritici* (ATCC 26517) using a procedure based on a Clinical and Laboratory Standards Institute (CLSI) microdilution assay protocol for filamentous fungi.

Stock solutions of the test compounds and standards were prepared in DMSO at 6400 µg/mL. Each stock solution was used to prepare a 2-fold dilution series ranging from 16 to 0.016 µg/mL (total of 11 compound concentrations) in RPMI-1640 (Roswell Park Memorial Institute) medium containing 3-(N-morpholino)propanesulfonic acid (MOPS) buffer and 2% DMSO. A 100 µL aliquot of the dilutions was added to columns 1 (16 µg/mL compound) through 11 (0.016 µg/mL compound) of a 96-well microtiter plate. This format was replicated in a second row of the microtiter plate. Thus, each microtiter plate could include 11 concentrations of four test or control compounds replicated twice. A 100 µL aliquot of RPMI-1640/MOPS/2% DMSO medium was added to column 12 (no compound control) of the microtiter plate.

A fresh culture of *S. tritici* was used to prepare a solution of approximately $5 \times 10^4$ colony-forming units per milliliter (cfu/mL) in RPMI/MOPS medium without DMSO. A 100 µL aliquot of this solution was added to all 96 wells in the microtiter plate. This results in final concentrations of each test or control compound of 8 µg/mL to 0.008 µg/mL in 200 µL of RPMI/MOPS media containing 1% DMSO and approximately $2.5 \times 10^4$ cfu/mL of *S. tritici*. The assay plates were incubated at 22° C. for seven days in the dark without shaking. The MIC for each compound was visually determined as the concentration which resulted in 50% reduction in the growth of *S. tritici* in comparison to the control (column 12).

In each case of Table 3 the rating scale is as follows:

| MIC (µg/mL) | Rating |
|---|---|
| ≤0.5 | A |
| >0.5-1.5 | B |
| >1.5-4 | C |
| >4 | D |
| Not tested | E |

TABLE 3

MIC Data for Compounds in Table 1

| Example Number | *Candida* MIC Rating | *Septoria* MIC Rating |
|---|---|---|
| 1 | A | A |
| 2 | A | E |
| 3 | A | C |
| 4 | A | A |
| 5 | A | A |
| 6 | A | C |
| 7 | A | A |
| 8 | A | B |
| 9 | A | A |
| 10 | A | A |
| 11 | A | A |
| 12 | A | E |
| 13 | E | E |
| 14 | E | E |
| 15 | A | C |
| 16 | A | A |
| 17 | E | E |
| 18 | A | A |
| 19 | E | E |
| 20 | D | C |
| 21 | C | D |
| 22 | C | D |
| 23 | A | C |
| 24 | A | B |
| 25 | A | A |
| 26 | A | B |
| 27 | A | A |
| 28 | A | A |
| 29 | A | C |
| 30 | A | A |
| 31 | A | B |
| 32 | A | B |
| 33 | A | B |
| 34 | A | A |
| 35 | A | A |
| 36 | A | A |
| 37 | A | A |
| 38 | A | A |
| 39 | C | E |
| 40 | A | A |
| 41 | A | A |
| 42 | A | D |
| 43 | A | E |
| 44 | A | B |
| 45 | A | A |
| 46 | B | A |
| 47 | A | B |
| 48 | C | E |
| 49 | C | E |
| 50 | C | E |
| 51 | A | C |
| 52 | C | E |
| 53 | B | C |
| 54 | C | E |
| 55 | A | C |
| 56 | C | E |

TABLE 3-continued

MIC Data for Compounds in Table 1

| Example Number | *Candida* MIC Rating | *Septoria* MIC Rating |
|---|---|---|
| 57 | A | C |
| 58 | A | E |

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A method of controlling a pathogen-induced disease in a plant that is at risk of being diseased from the pathogen comprising contacting one of the plant and an area adjacent to the plant with a composition of Formula (I) or a salt thereof, wherein:

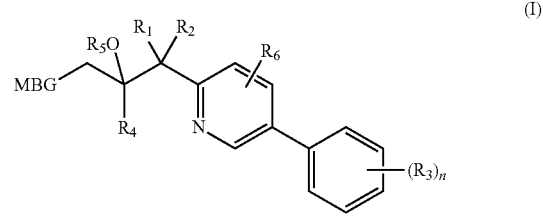

(I)

MBG is optionally substituted tetrazolyl, optionally substituted triazolyl, or optionally substituted pyrazolyl;
$R_1$ is H, halo, alkyl or haloalkyl;
$R_2$ is H, halo, alkyl or haloalkyl;
each $R_3$ is H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, $S(O)_2R_7$, nitro, $C(=O)CF_3$, $C(=O)OR_7$, $C(=O)NR_7R_8$, amino, or cyclic amino, $NHC(=O)CF_3$, or $OCF_2C(=O)OR_7$;
$R_4$ is aryl, heteroaryl, or cycloalkyl, optionally substituted with 0, 1, 2 or 3 independent $R_3$;
$R_5$ is H, $-P(O)(OH)_2$, $-CH_2-O-P(O)(OH)_2$, or $-C(O)$alkyl optionally substituted with amino;
$R_6$ is H, halo, alkyl, haloalkyl or haloalkoxy;
$R_7$ is alkyl or cycloalkyl;
$R_8$ is alkyl or haloalkyl; and
n is 0, 1,2 or 3.

2. The method of claim 1, wherein $R_1$ is fluoro.
3. The method of claim 1, wherein $R_2$ is fluoro.
4. The method of claim 1, wherein $R_1$ and $R_2$ are fluoro.
5. The method of claim 1, wherein $R_4$ is phenyl optionally substituted with 0, 1, 2 or 3 independent $R_3$.

6. The method of claim 1, wherein $R_4$ is phenyl optionally substituted with 0, 1, 2 or 3 independent halo.

7. The method of claim 1, wherein $R_4$ is phenyl optionally substituted with 0, 1, 2 or 3 fluoro.

8. The method of claim 1, wherein $R_4$ is 2,4-difluorophenyl.

9. The method of claim 1, wherein $R_5$ is H.

10. The method of claim 1, wherein $R_5$ is —P(O)(OH)$_2$, —CH$_2$—O—P(O)(OH)$_2$, or —C(O)alkyl optionally substituted with amino.

11. The method of claim 1, wherein:
$R_1$ is fluoro;
$R_2$ is fluoro;
$R_4$ is 2,4-difluorophenyl; and
$R_5$ is H.

12. The method of claim 11, wherein:
each $R_3$ is independently H, alkyl, cycloalkyl, cyano, haloalkyl, alkoxy, halo, haloalkoxy, alkoxyalkyl, haloalkoxyalkyl, aryloxyalkyl, thioalkyl, hydroxyl, halothioalkyl, thiocyanate, S(O)$_2$R$_7$, nitro, C(=O)CF$_3$, C(=O)OR$_7$, C(=O)NR$_7$R$_8$, amino, or cyclic amino, and
n is 1 or 2.

13. The method of claim 11, wherein:
each $R_3$ is independently alkoxyalkyl, haloalkoxyalkyl, aryloxyalkyl, thioalkyl, hydroxyl, halothioalkyl, thiocyanate, S(O)$_2$R$_7$, nitro, C(=O)CF$_3$, C(=O)OR$_7$, C(=O)NR$_7$R$_8$, amino, or cyclic amino, and
n is 1.

14. The method of claim 1, which is one of:
4-(6-(2-(2,4-Difluorophenyl)-1,1-difluoro-2-hydroxy-3-(1H-tetrazol-1-yl)propyl) pyridin-3-yl)benzonitrile (1);
2-(2,4-Difluorophenyl)-1,1-difluoro-3-(1H-tetrazol-1-yl)-1-(5-(4-(trifluoromethyl) phenyl)pyridin-2-yl)propan-2-ol (2);
3-(6-(2-(2,4-Difluorophenyl)-1,1-difluoro-2-hydroxy-3-(1H-tetrazol-1-yl)propyl)pyridin-3-yl)benzonitrile (3);
2-(2,4-Difluorophenyl)-1,1-difluoro-1-(5-(4-isopropoxyphenyl)pyridin-2-yl)-3-(1H-tetrazol-1-yl)propan-2-ol (4);
2-(2,4-Difluorophenyl)-1,1-difluoro-1-(5-(4-fluorophenyl)pyridin-2-yl)-3-(1H-tetrazol-1-yl)propan-2-ol (5);
2-(2,4-Difluorophenyl)-1,1-difluoro-3-(1H-tetrazol-1-yl)-1-(5-(3-(trifluoromethoxy)phenyl)pyridin-2-yl)propan-2-ol (6);
2-(2,4-Difluorophenyl)-1,1-difluoro-3-(1H-tetrazol-1-yl)-1-(5-(4-(trifluoromethoxy)phenyl)pyridin-2-yl)propan-2-ol (7);
1-(5-(3-Chlorophenyl)pyridin-2-yl)-2-(2,4-difluorophenyl)-1,1-difluoro-3-(1H-tetrazol-1-yl)propan-2-ol (8);
1-(5-(4-Chlorophenyl)pyridin-2-yl)-2-(2,4-difluorophenyl)-1,1-difluoro-3-(1H-tetrazol-1-yl)propan-2-ol (9);
2-(2,4-Difluorophenyl)-1-(5-(2,5-difluorophenyl)pyridin-2-yl)-1,1-difluoro-3-(1H-tetrazol-1-yl)propan-2-ol (10);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11);
2-(2,4-Difluorophenyl)-1,1-difluoro-1-(5-(4-(2,2,3,3,3-pentafluoropropoxy)phenyl)pyridin-2-yl)-3-(1H-tetrazol-1-yl)propan-2-ol (12);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate hydrochloride (13);
2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14);
2-(2,4-Difluorophenyl)-1, 1-difluoro-3-(1H-pyrazol-3-yl)-1-(5-(4-(trifluoro methoxy)phenyl)pyridin-2-yl)propan-2-ol (15);
2-(2,4-Difluorophenyl)-1,1-difluoro-1-(5-(4-fluorophenyl)pyridin-2-yl)-3-(1H-1,2,4-triazol-1-yl)propan-2-ol (16);
2-(2,4-Difluorophenyl)-1,1-difluoro-3-(1H-1,2,4-triazol-1-yl)-1-(5-(4-(2,2,2-trifluoroethoxy)phenyl)pyridin-2-yl)propan-2-ol (17);
2-(2,4-Difluorophenyl)-1,1-difluoro-3-(1H-1,2,4-triazol-1-yl)-1-(5-(4-(trifluoromethoxy)phenyl)pyridin-2-yl)propan-2-ol (18);
2-(2,4-Difluorophenyl)-1,1-difluoro-3-(1H-1,2,3-triazol-1-yl)-1-(5-(4-(trifluoromethoxy)phenyl)pyridin-2-yl)propan-2-ol (19);
2-(2,4-Difluorophenyl)-1,1-difluoro-3-(2H-tetrazol-2-yl)-1-(5-(4-(2,2,2-trifluoroethoxy)phenyl)pyridin-2-yl)propan-2-ol (20);
2-(2,4-Difluorophenyl)-1,1-difluoro-1-(5-(3-(fluorophenyl)pyridin-2-yl)-3-(2H-tetrazol-1-yl)propan-2-ol (21);
2-(2,4-Difluorophenyl)-1,1-difluoro-3-(2H-tetrazol-2-yl)-1-(5-(4-(trifluoromethylphenyl)pyridin-2-yl)propan-2-ol (22);
4-(6-(2-(2,4-Difluorophenyl)-1,1-difluoro-2-hydroxy-3-(1H-tetrazol-1-yl)propyl)pyridin-3-yl)phenol (23);
2-(2,4-Difluorophenyl)-1,1-difluoro-1-(5 -(3 -isopropylphenyl)pyridin-2-yl)-3 -(1H-tetrazol-1-yl)propan-2-ol (24);
2-(2,4-Difluorophenyl)-1-(5-(3,4-difluorophenyl)pyridin-2-yl)-1,1-difluoro-3-(1H-tetrazol-1-yl)propan-2-ol (25);
1-(5-(3-(Difluoromethoxy)phenyl)pyridin-2-yl)-2-(2,4-difluorophenyl)-1,1-difluoro-3-(1H-tetrazol-1-yl)propan-2-ol (26);
2-(2,4-Difluorophenyl)-1,1-difluoro-3-(1H-tetrazol-1-yl)-1-(5-(4-((trifluoromethyl)thio)phenyl)pyridin-2-yl)propan-2-ol (27)
1-(5-(4-(tert-Butoxy)phenyl)pyridin-2-yl)-2-(2,4-difluorophenyl)-1,1-difluoro-3-(1H-tetrazol-1-yl)propan-2-ol (28);
1-(5-(4-Chloro-3-fluorophenyl)pyridin-2-yl)-2-(2,4-difluorophenyl)-1,1-difluoro-3-(1H-tetrazol-1-yl)propan-2-ol (29);
3-(6-(2-(2,4-Difluorophenyl)-1,1-difluoro-2-hydroxy-3 -(1H-tetrazol-1-yl)propyl)pyridin-3-yl)phenol (30);
2-(2,4-Difluorophenyl)-1,1-difluoro-3-(1H-tetrazol-1-yl)-1-(5-(3-(trifluoromethyl)phenyl)pyridin-2-yl)propan-2-ol (31);
2-(2,4-Difluorophenyl)-1,1-difluoro-1-(5-(4-nitrophenyl)pyridin-2-yl)-3-(1H-tetrazol-1-yl)propan-2-ol (32);
1-(4-(6-(2-(2,4-Difluorophenyl)-1,1-difluoro-2-hydroxy-3-(1H-tetrazol-1-yl)propyl)pyridin-3-yl)phenyl)-2,2,2-trifluoroethanone (33);
2-(4-Chloro-2-fluorophenyl)-1,1-difluoro-3-(1H-tetrazol-1-yl)-1-(5-(4-(trifluoromethoxy)phenyl)pyridin-2-yl)propan-2-ol (34);
2-(2,4-Difluorophenyl)-1,1-difluoro-1-(5-phenylpyridin-2-yl)-3-(1H-tetrazol-1-yl)propan-2-ol (35);
2-(2,4-Difluorophenyl)-1,1-difluoro-1-(5-(4-morpholinophenyl)pyridin-2-yl)-3-(1H-tetrazol-1-yl)propan-2-ol (36);
N-(4-(6-(2-(2,4-Difluorophenyl)-1,1-difluoro-2-hydroxy-3-(1H-tetrazol-1-yl)propyl)pyridin-3-yl)phenyl)-2,2,2-trifluoroacetamide (37);
1-(5-(4-(Difluoromethoxy)phenyl)pyridin-2-yl)-2-(2,4-difluorophenyl)-1,1-difluoro-3-(1H-tetrazol-1-yl)propan-2-ol (38);

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (39);

1-(5-(4-(((Difluoromethyl)thio)phenyl)pyridin-2-yl)-2-(2,4-difluorophenyl)-1,1-difluoro-3-(1H-tetrazol-1-yl)propan-2-ol (40);

2-(2,4-Difluorophenyl)-1,1-difluoro-3-(1H-tetrazol-1-yl)-1-(5-(4-(2,2,2-trifluoroethyl)phenyl)pyridin-2-yl)propan-2-ol (41);

4-(6-(2-(2,4-Difluorophenyl)-1,1-difluoro-2-hydroxy-3-(1H-tetrazol-1-yl)propyl)pyridin-3-yl)-N-methylbenzamide (42);

Ethyl 2-(4-(6-(2-(2,4-difluorophenyl)-1,1-difluoro-2-hydroxy-3 -(1H-tetrazol-1-yl)propyl)pyridin-3 -yl)phenoxy)-2,2-difluoroacetate (43);

2-(2,4-Difluorophenyl)-1,1-difluoro-3-(1H-tetrazol-1-yl)-1-(5-(4-(3,3,3-trifluoropropoxy)phenyl)pyridin-2-yl)propan-2-ol (44);

2-(2,4-Difluorophenyl)-1,1-difluoro-3-(1H-tetrazol-1-yl)-1-(5-(4-((2,2,2-trifluoroethyl)thio)phenyl)pyridin-2-yl)propan-2-ol (45);

2-(2,4-Difluorophenyl)-3-fluoro-1-(1H-tetrazol-1-yl)-3 -(5-(4-(trifluoromethoxy)phenyl)pyridin-2-yl)butan-2-ol (46 and 47);

2-(2,4-Difluorophenyl)-3 -fluoro-3-(5-(4-fluorophenyl)pyridin-2-yl)-1-(2H-tetrazol-2-yl)butan-2-ol (48 and 49);

2-(2,4-Difluorophenyl)-3-fluoro-3-(5-(4-fluorophenyl)pyridin-2-yl)-1-(1H-tetrazol-1-yl)butan-2-ol (50 and 51);

2-(2,4-Difluorophenyl)-3-fluoro-1-(1H-tetrazol-1-yl)-3 -(5-(4-(trifluoromethyl)phenyl)pyridin-2-yl)butan-2-ol (52 and 53);

3-(5-(4-Chlorophenyl)pyridin-2-yl)-2-(2,4-difluorophenyl)-3-fluoro-1-(1H-tetrazol-1-yl)butan-2-ol (54 and 55);

2-(2,4-Difluorophenyl)-3-fluoro-1-(1H-tetrazol-1-yl)-3-(5-(4-(2,2,2-trifluoroethoxy)phenyl)pyridin-2-yl)butan-2-ol (56 and 57); or 2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl dihydrogen phosphate (58).

15. The method of claim 1, wherein the pathogen inducing the disease is a fungal pathogen.

16. The method of claim 1, wherein the composition further comprises an insecticide.

17. The method of claim 1, wherein the composition further comprises a weed control agent.

18. The method of claim 1, wherein the pathogen inducing the disease is a plant fungal pathogen belonging to at least one genera selected from *Blumeria, Podosphaera, Sphaerotheca, Uncinula, Erysiphe, Puccinia, Phakopsora, Gymnosporangium, Hemileia, Uromyces, Alternaria, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminthosporium, Stagonospora, Exserohilum*, and *Pyricularia*.

19. The method of claim 1, wherein the disease is one of apple scab, speckled leaf blotch of wheat, leaf spot of sugarbeets, leaf spot of peanut, cucumber anthracnose, wheat leaf rust, grape powdery mildew, wheat powdery mildew, and black sigatoka.

20. The method of claim 1, wherein the pathogen is one of *Venturia inaequalis, Septoria tritici, Cercospora beticola, Cercospora arachidicola, Colletotrichum lagenarium, Puccinia graminis f. sp. tritici, Uncinula necator, Blumeria graminis*, and *Mycosphaerella fijiensis*.

21. The method of claim 1, wherein the composition includes an agriculturally acceptable carrier.

\* \* \* \* \*